(12) United States Patent
Aoki et al.

(10) Patent No.: US 8,721,854 B2
(45) Date of Patent: May 13, 2014

(54) CONTROL DEVICE FOR EXHAUST GAS SENSOR OF INTERNAL-COMBUSTION ENGINE

(75) Inventors: Keiichiro Aoki, Susono (JP); Yusuke Suzuki, Susono (JP); Yoshihiro Sakayanagi, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 1744 days.

(21) Appl. No.: 10/880,554

(22) Filed: Jul. 1, 2004

(65) Prior Publication Data

US 2005/0029098 A1    Feb. 10, 2005

(30) Foreign Application Priority Data

Aug. 4, 2003    (JP) ................................. 2003-285816

(51) Int. Cl.
*G01N 27/00*    (2006.01)

(52) U.S. Cl.
USPC ........................................................ 204/410

(58) Field of Classification Search
USPC ........................................................ 204/410
See application file for complete search history.

(56) References Cited

U.S. PATENT DOCUMENTS

| 5,518,600 | A | * | 5/1996 | Uchinami ...................... 204/401 |
| 6,084,418 | A | * | 7/2000 | Takami et al. ................. 324/717 |
| 6,258,232 | B1 | * | 7/2001 | Hasegawa et al. ............. 204/424 |
| 6,397,659 | B1 | * | 6/2002 | Mizoguchi et al. ............ 73/23.2 |

FOREIGN PATENT DOCUMENTS

| JP | A 6-342946 | 12/1994 |
| JP | A-08-005605 | 1/1996 |
| JP | A 9-101285 | 4/1997 |
| JP | A 9-274006 | 10/1997 |
| JP | A 9-292364 | 11/1997 |
| JP | A 2001-13106 | 1/2001 |

* cited by examiner

*Primary Examiner* — Jennifer Michener
*Assistant Examiner* — Dustin Q Dam
(74) *Attorney, Agent, or Firm* — Oliff PLC

(57) ABSTRACT

Disclosed is a control device, which controls an air-fuel ratio sensor that is mounted in an exhaust path of an internal-combustion engine. The air-fuel ratio sensor is capable of pumping oxygen in a gas. Normally (time t0-t1, time t3 or later), a positive voltage Vp1 is applied to a sensor element (FIG. 7A), and the air-fuel ratio is calculated (FIG. 7C) in accordance with a sensor current (FIG. 7B). A heater is driven after internal-combustion engine startup to heat the sensor element. In a process in which the sensor element temperature rises, a negative voltage Vm, which is oriented in a direction different from that of the positive voltage Vp1, is applied to the sensor element.

11 Claims, 12 Drawing Sheets

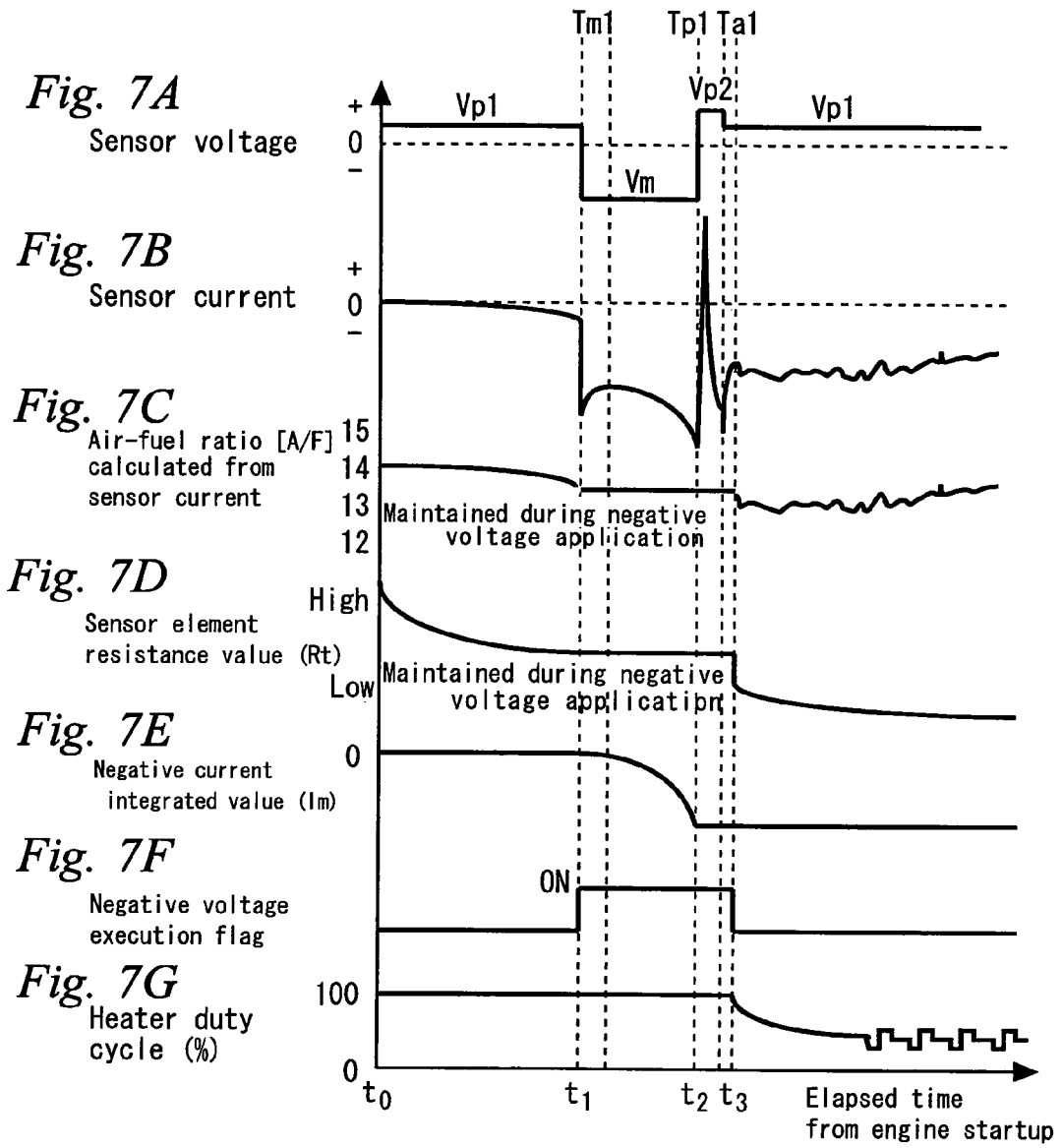

CONTROL DEVICE FOR EXHAUST GAS SENSOR OF INTERNAL-COMBUSTION ENGINE

BACKGROUND OF THE INVENTION

1. Field of the Invention

The present invention relates to a control device for an exhaust gas sensor of internal-combustion engine, and more particularly to a control device suitable for controlling an exhaust gas sensor that is equipped with a sensor element having a function for pumping oxygen in a gas.

2. Background Art

A device for controlling an air-fuel ratio sensor, which is positioned in an exhaust path of an internal-combustion engine, is disclosed by Japanese Patent Laid-open No. Hei 9-101285. This device applies a predetermined positive voltage to the air-fuel ratio sensor's sensor element during an internal-combustion engine's operation. In this instance, the sensor element pumps oxygen in an exhaust gas, and causes an electrical current to flow in accordance with the amount of such pumping, that is, invokes the flow of a limiting current corresponding to the oxygen concentration in the exhaust gas. The oxygen concentration in the exhaust gas corresponds to the air-fuel ratio of the exhaust gas. Therefore, when the above-mentioned conventional configuration is employed, the air-fuel ratio of the exhaust gas can be detected in accordance with the electrical current flow in the sensor element.

The above sensor element has an electrode that is exposed to an exhaust gas and an electrode that is exposed to atmospheric air. When the sensor element is used, oxygen is combined with the electrode that is exposed to atmospheric air. When the degree of such combination increases, the resistance of the sensor element increases, then the characteristic of the air-fuel ratio sensor deteriorates. To achieve recovery from such deterioration, the above conventional device applies a negative voltage, which is oriented in a direction opposite to that of a normally applied positive voltage, to the sensor element during fuel cut of an internal-combustion engine. While the fuel cut is being performed, there is no need to detect the air-fuel ratio. Therefore, a negative voltage can be applied to the sensor element at such timing without decreasing the control accuracy of the air-fuel ratio.

When a negative voltage is applied to the sensor element that is adequately warmed up, the oxygen combined with the electrode exposed to atmospheric air leaves the electrode and moves toward the other electrode. Therefore, when the above conventional configuration is employed, the sensor element can achieve recovery as needed from deterioration during an internal-combustion engine operation, thereby making it possible to maintain adequate detection accuracy of the air-fuel ratio sensor.

It is generally known that the air-fuel ratio sensor element and the like generate a stable output when heated to a predetermined activity temperature after internal-combustion engine startup. To obtain an excellent emission characteristic in an internal-combustion engine, it is preferred that the time interval between the instant at which the internal-combustion engine is started and the instant at which the exhaust gas sensor generates a stable output be minimized. However, the conventional device described above attempts to achieve sensor characteristic restoration in synchronism with fuel cut sequence execution after the end of internal-combustion engine warm-up. That is, the conventional device does not reduce the period of time that is required for the exhaust gas sensor to generate a stable output after the internal-combustion engine startup.

SUMMARY OF THE INVENTION

The present invention has been made to solve the above problems, and provides a control device that is used with an exhaust gas sensor of internal-combustion engine and capable of reducing the time interval between the instant at which the internal-combustion engine starts up and the instant at which the exhaust gas sensor generates a stable output.

The above object of the present invention is achieved by a control device for an exhaust gas that is to be mounted in an exhaust path of an internal-combustion engine. The exhaust gas sensor is equipped with a sensor element having a function for pumping oxygen in a gas. The control device includes positive voltage application unit for applying a positive voltage to the sensor element. The control unit also includes a sensor current detection unit for detecting a sensor current flow through the sensor element. A sensor output acquisition unit is also provided in the control device for acquiring a sensor current flow prevailing upon application of the positive voltage as a sensor output. The control unit further includes a negative voltage application unit for applying a negative voltage, which is a reversal of the positive voltage, to the sensor element during a warm-up process for the sensor element.

Other objects and further features of the present invention will be apparent from the following detailed description when read in conjunction with the accompanying drawings.

BRIEF DESCRIPTION OF THE DRAWINGS

FIGS. 7A to 7G are timing charts describing a flow of control executed by the control device of the first embodiment;

BEST MODE OF CARRYING OUT THE INVENTION

First Embodiment

[Hardware Configuration of the First Embodiment]

Figure 1:
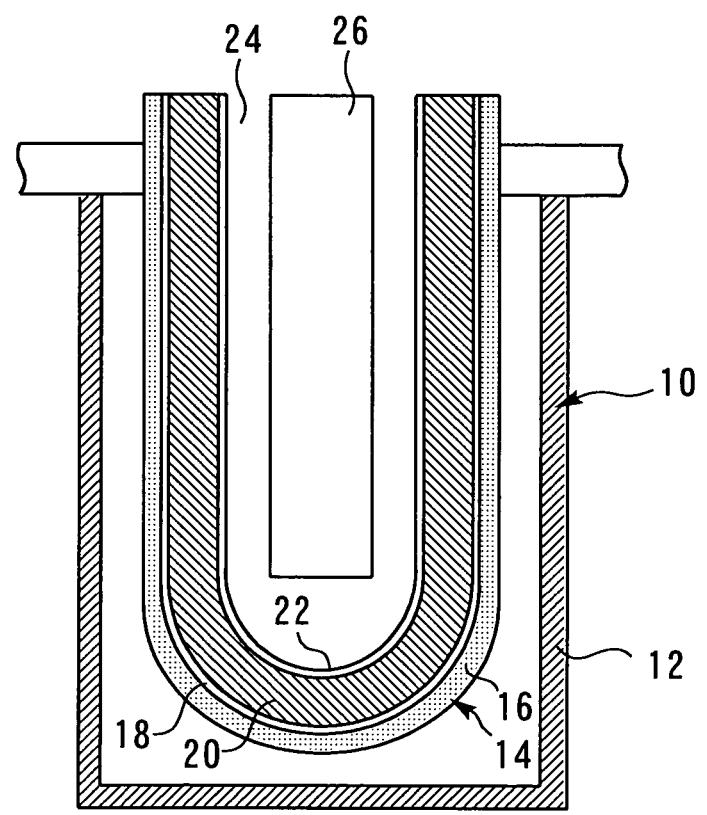
FIG. 1 illustrates a configuration of an air-fuel ratio sensor that is used in a first embodiment of the present invention.

FIG. 1 illustrates the configuration of an air-fuel ratio sensor 10 that is used in a first embodiment of the present invention. The air-fuel ratio sensor 10 shown in FIG. 1 is positioned in an internal-combustion engine's exhaust path and used to detect the air-fuel ratio of the exhaust gas. The air-fuel ratio sensor 10 is provided with a cover 12. The cover 12 is mounted in the exhaust path in such a manner that it is exposed to the exhaust gas.

The cover 12 is provided with a hole (not shown) for introducing the exhaust gas inward. A sensor element 14 is positioned inside the cover 12. The sensor element 14 has a tubular structure whose one end (lower end in FIG. 1) is closed. The outer surface of the tubular structure is covered with a diffused resistor layer 16. The diffused resistor layer 16 is made of alumina or other heat-resistant porous substance. It controls the diffusion speed of the exhaust gas near the surface of the sensor element 14.

The inside of the diffused resistor layer 16 is provided with an exhaust-side electrode 18, a solid electrolyte layer 20, and an atmospheric-air-side electrode 22. The exhaust-side electrode 18 and atmospheric-air-side electrode 22 are made of Pt or other highly catalytic, precious metal. These electrodes are electrically connected to a control circuit, which will be described later. The solid electrolyte layer 20 is a sintered body that contains $ZrO_2$ or the like. It characteristically conducts oxygen ions.

An atmospheric chamber 24, which is exposed to atmospheric air, is formed inside the sensor element 14. A heater 26 for heating the sensor element 14 is mounted in the atmospheric chamber 24. The sensor element 14 exhibits a stable output characteristic at an activity temperature of approximately 700° C. The heater 26 is electrically connected to a control circuit, which will be described later. The control circuit exercises control so that the sensor element 14 is heated and maintained at an appropriate temperature.

Figure 2:
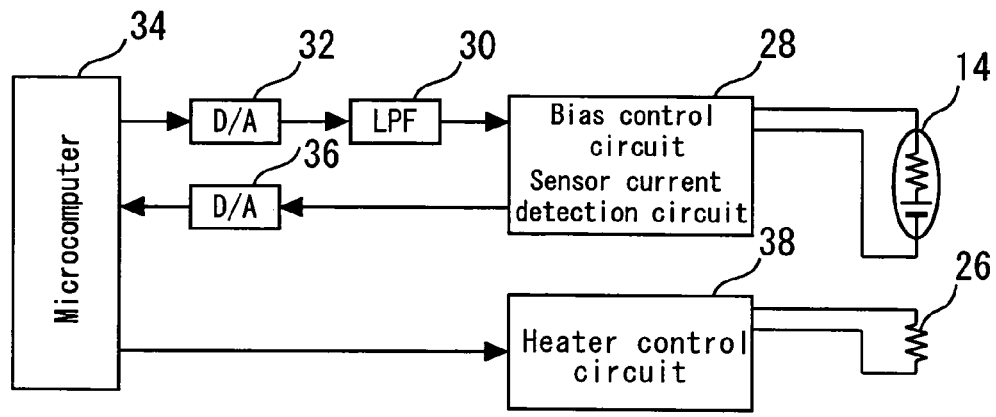
FIG. 2 is a block diagram illustrating a configuration of a control device for the air-fuel ratio sensor of the first embodiment.

FIG. 2 is a block diagram illustrating the configuration of a control device for the air-fuel ratio sensor 10. As shown in FIG. 2, the sensor element 14 can be equivalently expressed with a resistance component and electromotive component. Further, the heater 26 can be equivalently expressed with a resistance component. A sensor element drive circuit 28 is connected to the sensor element 14. The sensor element drive circuit 28 includes a bias control circuit for applying a desired voltage to the sensor element 14 and a sensor current detection circuit for detecting a current flow in the sensor device 14. The configuration of these circuits will be described in detail later with reference to FIG. 3.

A microcomputer 34 is connected to the bias control circuit, which is included in the sensor element control circuit 28, via a low-pass filter (LPF) 30 and a D/A converter 32. The microcomputer 34 can issue an instruction, through above described path, to the bias control circuit for specifying the voltage to be applied to the sensor element 14. The microcomputer 34 is connected via the D/A converter 36 to the sensor current detection circuit, which is provided in the sensor element control circuit 28. The microcomputer 34 can read a detected sensor current value through the above described path.

A heater control circuit 38 is connected to the heater 26. The microcomputer 34 is connected to the heater control circuit 38. Upon receipt of an instruction from the microcomputer 34, the heater control circuit 38 supplies a drive signal to the heater 26 in compliance with the instruction, thereby causing the heater 26 to generate a desired amount of heat.

Figure 3:
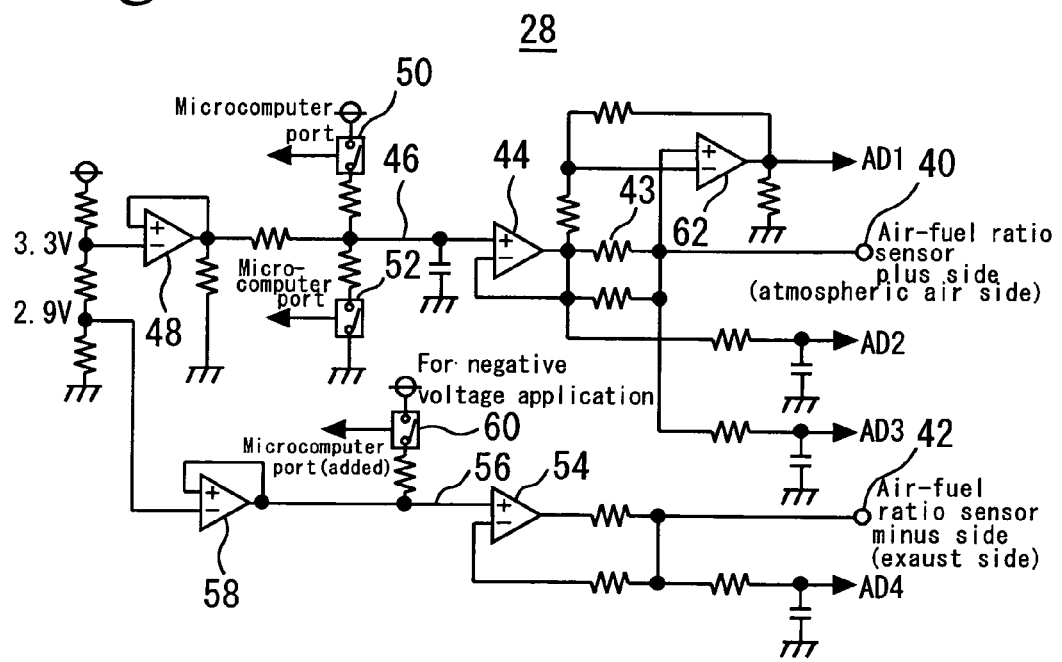
FIG. 3 is a typical circuit diagram of a sensor element control circuit provided in the control device of the first embodiment.

FIG. 3 is a typical circuit diagram of the sensor element control circuit 28, which is shown in FIG. 2. This circuit has a positive terminal 40, which is to be connected to the atmospheric-air-side electrode 22 of the air-fuel ratio sensor 10, and a negative terminal 42, which is to be connected to the exhaust-side electrode 18 of the air-fuel ratio sensor 10. A sensor current detection resistor 43 is connected to the positive terminal 40. A positive voltage line 46 is connected to the sensor current detection resistor 43 via buffer circuit 44. A constant potential of 3.3 V is supplied to the positive voltage line 46 via buffer circuit 48. Further, the positive voltage line 46 is connected to a switch circuit 50 for raising the line's potential to a power supply potential and connected to a switch circuit 52 for lowering the line's potential down to a ground potential.

Switch circuits 50 and 52 are both connected to the microcomputer 34 via microcomputer ports. If switch circuits 50 and 52 are both turned OFF, the positive terminal 40 is at a reference potential that corresponds to a potential of 3.3 V If switch circuit 50 is turned ON, the potential of the positive terminal 40 becomes higher than the reference potential. If, on the other hand, switch circuit 52 is turned ON, the potential becomes lower than the reference potential. As described above, the circuit shown in FIG. 3 makes it possible to selectively introduce the reference potential, a potential higher than the reference potential, or a potential lower than the reference potential to the positive terminal 40 by controlling the status of switch circuits 50 and 52.

A negative voltage line 56 is connected to the negative terminal 42 of the sensor element control circuit 28 via buffer circuit 54. A constant voltage of 2.9 V is supplied to the negative voltage line 56 via buffer circuit 58. The negative voltage line 56 is also connected to switch circuit 60, which raises the potential of the line to a supply voltage.

Switch circuit 60 is connected to the microcomputer 34 via a microcomputer port. If switch circuit 60 is turned OFF, the negative terminal 42 is at a low-voltage-side reference potential that corresponds to a potential of 2.9 V The low-voltage-side reference potential is lower than a reference potential that is developed at the positive terminal 40. Under these circumstances, therefore, a predetermined voltage, which is directed from the atmospheric-air-side electrode 22 to the exhaust-side electrode 18, is applied to the sensor element 14. This voltage is hereinafter referred to as the "positive voltage".

If switch circuit 50 is turned ON while switch circuit 60 is OFF, the voltage applied to the sensor element 14 rises above the positive voltage because the potential of the positive terminal 40 increases. The resulting applied voltage is hereinafter referred to as the "impedance measurement voltage". If, on the other hand, switch circuit 52 is turned ON while switch circuit 60 is OFF, the potential developed at the positive terminal 40 becomes lower than that of the negative terminal 42. As a result, a voltage that is oriented in a direction opposite to that of the positive voltage is applied to the sensor element 14. The resulting applied voltage is hereinafter referred to as the "impedance measurement negative voltage".

If switch circuit 60 is turned ON within the circuit shown in FIG. 3 in a situation where the reference potential is introduced to the positive terminal 40, the potential developed at the negative terminal 42 exceeds the reference potential. As a result, a voltage that is oriented in a direction opposite to that of the positive voltage is applied to the sensor element 14. The resulting applied voltage is hereinafter referred to as the "negative voltage". If an excessive voltage is applied to the solid electrolyte layer 20, which composes the sensor element 14, the internal oxygen is ionized and the resulting ionized oxygen flows. The solid electrolyte layer 20 is then blackened (this phenomenon is called "blackening"). In the present embodiment, the above negative voltage is limited to a level lower than 2V for the purpose of avoiding such blackening.

In the circuit shown in FIG. 3, the current flowing in the sensor current detection resistor 43 can be handled as being equal to the current flowing in the sensor element 14 (sensor current). The positive and negative terminals of a differential amplifier circuit 62 are connected across the sensor current detection resistor 43. The output terminal of the differential amplifier circuit 62 is connected to the microcomputer 34 via an AD1 port. In the configuration described above, an output that is obtained by amplifying the voltage across the sensor current detection resistor 43 by a predetermined gain appears at the AD1 port. The voltage across the sensor current detection resistor 43 corresponds to the current flowing across the sensor current detection resistor 43, that is, the sensor current. Therefore, this circuit can detect the sensor current at a predetermined gain by reading the potential of the AD1 port.

An AD2 port and an AD3 port are connected across the sensor current detection resistor 43 via a smoothing circuit. A potential corresponding to the current flowing in the sensor current detection resistor 43 is generated between the AD2 port and AD3 port. According to the sensor element control circuit 28 shown in FIG. 3, the signal corresponding to the current flow in the sensor element 14 can therefore be obtained without any amplification, that is, at a gain of 1, by detecting the difference between the AD2 port potential and AD3 port potential. As described above, the sensor element control circuit 28 shown in FIG. 2 can generate two types of signals, which differ in gain, as signals representing a sensor current. Consequently, the microcomputer 34 can detect the sensor current with high accuracy over a wide range, from a very small sensor current to a large sensor current.

The negative terminal 42 of the sensor element control circuit 28 is connected to an AD4 port via a smoothing circuit. Meanwhile, the positive terminal 40 of the sensor element control circuit 28 is connected to the above AD3 port via a smoothing circuit. The potentials of the negative terminal 42 and positive terminal 40 appear respectively at these ports. Therefore, the microcomputer 34 can actually detect the voltage applied to the sensor element 14 by detecting the difference between the potential developed at the AD3 port and the potential developed at the AD4 port.

[Basic Operation of the Device According to the First Embodiment]

The control device according to the present embodiment has a function for detecting the exhaust gas air-fuel ratio in accordance with the output from the air-fuel ratio sensor 10 (air-fuel ratio detection function) and functions for detecting the element impedance Rt of the sensor element 14 and controlling the heater 26 in accordance with the value Rt (impedance detection function and heater control function).

Figure 4:
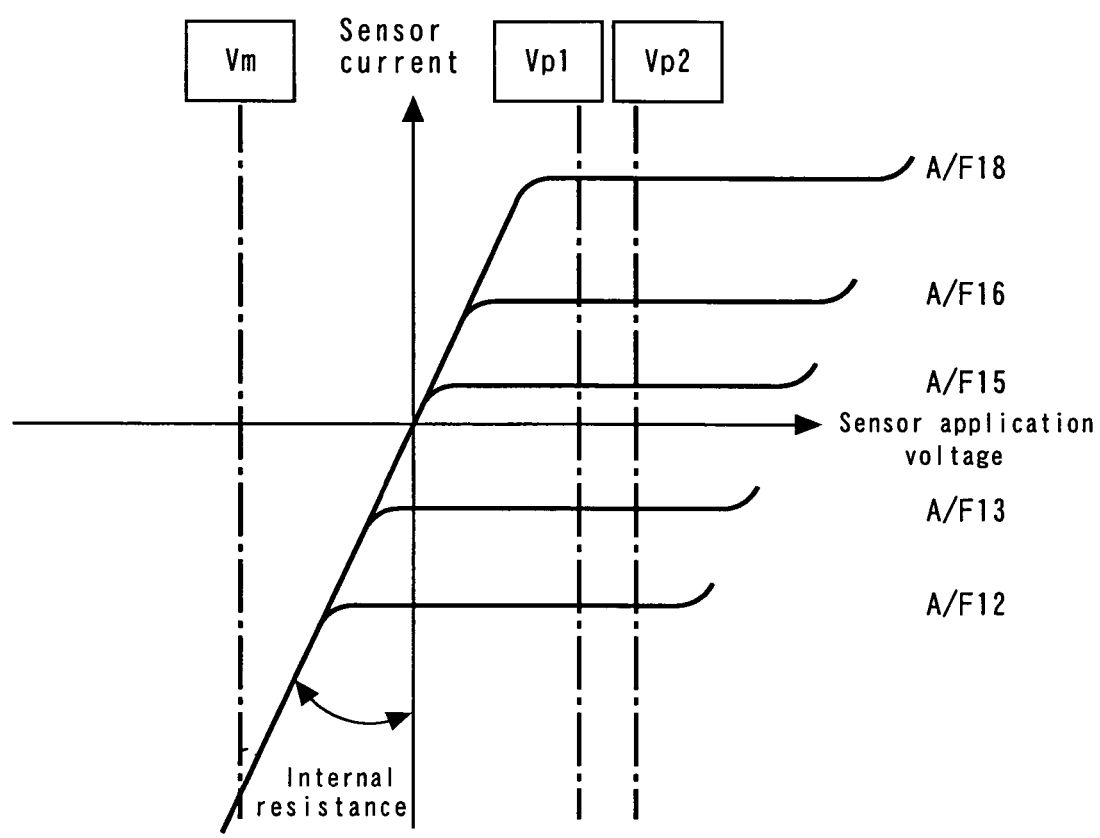
FIG. 4 illustrates a characteristic of a sensor element provided in the air-fuel ratio sensor.

FIG. 4 illustrates the characteristic of the sensor element 14 that prevails in a situation where the activity temperature is reached. The applied voltage, which is plotted along the horizontal axis, is indicated in such a manner that its value is "positive" when the potential of the atmospheric-air-side electrode 22 is higher than that of the exhaust-side electrode 18. The sensor current, which is plotted along the vertical axis, is indicated so that its value 18 is "positive" when the current flows from the atmospheric-air-side electrode 22 to the exhaust-side electrode.

As shown in FIG. 4, the sensor element 14 has a characteristic that varies the sensor current in accordance with the applied voltage and the exhaust gas air-fuel ratio A/F. More specifically, the sensor element 14 varies the sensor current substantially in proportion to the applied voltage when the applied voltage is sufficiently low, and converges the sensor current to a limiting current corresponding to the exhaust air-fuel ratio A/F as the applied voltage increases.

When implementing the air-fuel ratio detection function, the control device according to the present embodiment turns OFF switch circuits 50, 52, and 60 and applies the above positive voltage to the sensor element 14. An applied voltage designated as Vp1 in FIG. 4 corresponds to the positive voltage. In this instance, the sensor current value corresponds to the exhaust air-fuel ratio A/F. Therefore, the microcomputer 34 can detect the exhaust air-fuel ratio A/F by reading the AD1 port's output, that is, implement the air-fuel ratio detection function.

The designation "Vp2" in FIG. 4 represents a "positive voltage for restoration", which may be applied to the sensor element 14 when a negative voltage application termination process is performed as described later. The "positive voltage for restoration" can be generated, for instance, by controlling switch circuit 50 appropriately. The designation "Vm" in FIG. 4 represents a "negative voltage" that can be applied to the sensor element 14 by turning ON switch circuit 60. As indicated in the figure, the absolute value of the sensor current arising upon application of the negative voltage Vm is sufficiently greater than that of the sensor current arising upon application of the positive voltage Vp1. As described earlier, the sensor element control circuit 28 shown in FIG. 3 can generate two sensor-current-indicating signals at different gains. The microcomputer 34 achieves detection by acquiring a signal having a great gain as regards a sensor current generated with the application of the positive voltage Vp1, and achieves detection by acquiring a signal having a small gain as regards a sensor current generated with the application of negative voltage Vm. Therefore, the control device according to the present embodiment can accurately detect the sensor current at high sensitivity under any situation although the sensor current absolute value with the application of positive voltage Vp1 greatly differs from the sensor current absolute value with the application of negative voltage Vm.

The microcomputer 34 implements the impedance detection function by periodically turning ON/OFF switch circuits 50 and 52 while implementing the air-fuel ratio detection function by the above method. More specifically, for implementing the impedance detection function, switch circuits 50 and 52 are sequentially turned ON in that order or in reverse order. When such an ON/OFF process is performed, the voltage applied to the sensor element 14 increases and decreases so that the sensor current and applied voltage vary while maintaining their proportional relationship. While the sensor current is proportional to the applied voltage, the element impedance Rt of the sensor element 14 can be detected from the ratio of their changes. Further, the circuit shown in FIG. 3 can detect the actual applied voltage from the outputs of the AD3 port and AD4 port and detect the sensor current from the output of the AD1 port. Therefore, the microcomputer 34 can periodically implement the impedance detection function by reading the outputs of the AD1 to AD4 ports in synchronism with the ON/OFF process for switch circuits 50 and 52.

The element impedance Rt significantly correlates with the temperature of the sensor element 14. Therefore, the element impedance Rt can be handled as a temperature characteristic value of the sensor element 14. In the present embodiment, the microcomputer 34 memorizes a target impedance that corresponds to a target activity temperature, and controls the electrical power supply to the heater 26 in such a manner that the actual element impedance Rt coincides with the target impedance. As a result, the device according to the present embodiment can exercise accurate control to maintain the sensor element 14 at a temperature close to the target activity temperature (heater control function).

[Necessity for Negative Voltage Application Control]

The necessity for negative voltage application control, which is characteristic of the device according to the present embodiment, will now be described. The air-fuel ratio A/F, which is detected by the air/fuel ratio sensor 10, is used for fuel injection quantity feedback control. More specifically, air-fuel ratio feedback control for adjusting the fuel injection quantity is exercised in the internal-combustion engine so that the detected air-fuel ratio A/F coincides with a target air-fuel ratio. This control operation significantly affects the emission characteristic of the internal-combustion engine. It is therefore preferred that the control operation starts immediately after internal-combustion engine startup.

However, the sensor element 14 needs to be heated to an activity temperature in order to ensure that the air-fuel ratio sensor 10 generates a stable output. To this end, it is common to start applying electrical power to the heater 26 simultaneously with engine startup, wait until the sensor element 14 reaches its activity temperature, and then start exercising air-fuel ratio feedback control as a process to be performed immediately after internal-combustion engine startup. In the warm-up process, the output of the air-fuel ratio sensor 10 tends to temporarily shift toward the rich side in relation to the real exhaust air-fuel ratio A/F and then agree with the real A/F value as the warm-up process progresses.

It is conceivable that the above-mentioned sensor output rich displacement in the warm-up process may be caused by adsorbable species, which is chemically combined with the surface of the sensor element 14 when it is cooled after the internal-combustion engine stops. Even after the internal-combustion engine stops, various exhaust gas components remain in the exhaust path to which the air-fuel ratio sensor 10 is exposed. When the temperature of the sensor element 14 is lowered from an activity temperature of approximately 700° C. to room temperature, the remaining components may chemically combine with the surface of the sensor element 14.

When the internal-combustion engine restarts and the sensor element 14 is heated to its reaction induction temperature, the adsorbable species, which is combined with the surface of the sensor element 14 as described above, begins to desorb from the surface of the sensor element 14. In this instance, the surface of the sensor element 14 is surrounded by a reduction atmosphere, that is, an atmosphere in which oxygen is insufficient, due to the influence of the desorbed adsorbable species. As a result, the output of the sensor element 14 is shifted toward the rich side from the real air-fuel ratio. The entire adsorbable species completes its desorption by the time the warm-up process for the sensor element 14 terminates. Therefore, the sensor output rich displacement, which occurs in the warm-up process, decreases as the sensor temperature approaches the activity temperature. It virtually disappears when the warm-up process for the sensor element 14 terminates.

The sensor output rich displacement, which arises due to the influence of the adsorbable species, almost converges by the time the warm-up process ends as described above. Therefore, air-fuel ratio feedback control, which is exercised subsequently, can be accurately completed under normal conditions without considering the influence of the adsorbable species. However, an unduly large amount of adsorbable species could be adsorbed by the sensor element 14 depending on the condition prevailing when the internal-combustion engine stops. When the engine restarts later in the above situation, the adsorbable species may not entirely become desorbed by the time the warm-up process for the sensor element 14 ends so that the sensor output may subsequently suffer rich displacement. To avoid such a condition, it is preferred that the warm-up process for the sensor element 14 be performed so as to reduce the period of time during which the sensor output may suffer rich displacement. If the period of time during which the sensor output may shift toward the rich side due to the adsorbable species is reduced, the sensor output can be used at an earlier time. As a result, it is possible to reduce the time interval between the instant at which the internal-combustion engine starts up and the instant at which air-fuel ratio feedback starts.

Figure 5:
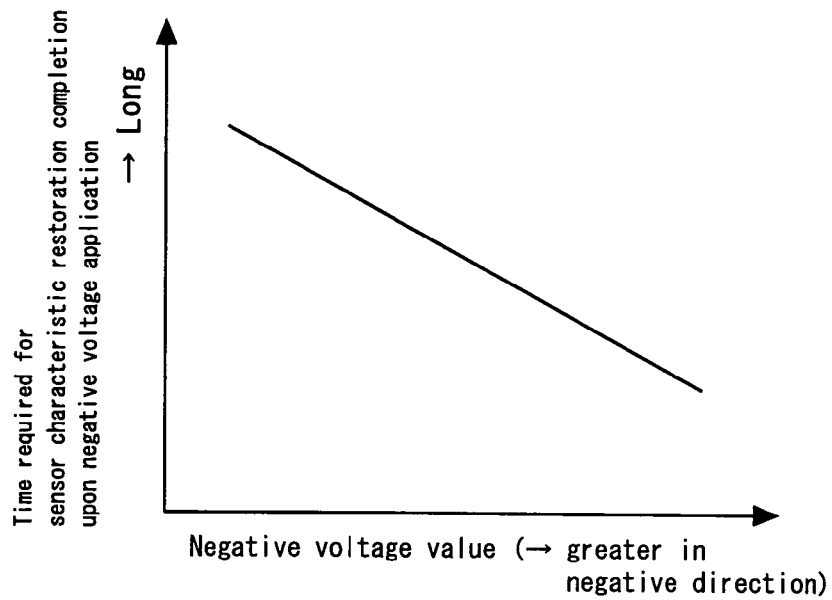
FIG. 5 illustrates relationship between time required for rich displacement annihilation and value of a negative voltage applied to the sensor element provided in the air-fuel ratio sensor.
Figure 6:
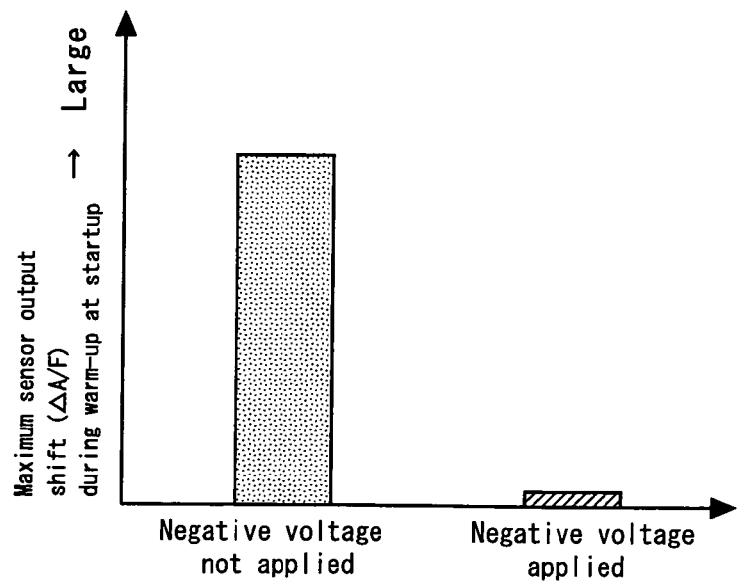
FIG. 6 relates to magnitude of rich displacement, which occurs in an output of the air-fuel ratio sensor, and shows comparison result between a case where negative voltage is applied and a case where the negative voltage is not applied.

FIG. 5 illustrates the relationship between the time required for rich displacement annihilation and the value of a voltage (oriented in negative direction) that is oriented from the exhaust-side electrode 18 to the atmospheric-air-side electrode 22 and applied in the warm-up process for the sensor element 14. FIG. 6 relates to the magnitude of rich displacement ($\Delta$A/F), which occurs during the sensor element warm-up process, and shows the comparison between a case where the above negatively-oriented voltage is not applied and a case where the above negatively-oriented voltage is applied.

When the warm-up process for the sensor element 14 progresses while a negatively-oriented voltage, which is oriented from the exhaust-side electrode 18 to the atmospheric-air-side electrode 22, is applied, an oxygen ion pumping process by the atmospheric-air-side electrode 22 starts at a time when the sensor element is heated to a temperature of approximately 300 to 350° C., that is, to a temperature at which the atmospheric-air-side electrode 22 begins to perform its catalytic action. Oxygen ions pumped in this manner move toward the exhaust-side electrode 18 and neutralize a reducing substance near the surface of the exhaust-side electrode 18. In other words, the oxygen ions conveyed close to the surface of the exhaust-side electrode 18 urge the adsorbable species, which is generated during the warm-up process for the sensor element 14, to become desorbed, and neutralize the desorbed substance. As a result, the time required for sensor element rich displacement annihilation decreases with an increase in the applied negative voltage as shown in FIG. 5. Further, the magnitude $\Delta$A/F of rich displacement, which occurs in the sensor output, is significantly smaller when the negative voltage is applied than when the negative voltage is not applied, as shown in FIG. 6.

As described above, sensor output rich displacement in the warm-up process for the sensor element 14 can be effectively reduced by applying a negative voltage to the sensor element 14 in its warm-up process. After the warm-up process for the sensor element 14 is started, therefore, the present embodiment applies an appropriate negative voltage to the sensor element 14 within a range that is valid for rich displacement inhibition and early termination.

[Flow of Air-fuel Ratio Sensor Control]

FIGS. 7A to 7G are timing diagrams illustrating the flow of a control operation that the control device according to the present invention performs for the air-fuel ratio sensor 10. The timing diagrams shown in FIGS. 7A to 7G show an operation that is performed after internal-combustion engine startup in a situation where an air-fuel mixture supplied to the internal-combustion engine is in a predefined rich air-fuel ratio because of start enrichment.

In FIGS. 7A to 7G, the time t0 is an internal-combustion engine startup time. The period between the time t1 and time t3 is a negative voltage application control execution period. As indicated by FIG. 7G, the control device according to the present embodiment starts applying electrical power to the heater 26 at a 100% duty ratio simultaneous with the internal-combustion engine starts up. The operation performed for driving the heater 26 at a 100% duty ratio continues until negative voltage application control terminates at the time t3. As a result, the temperature of the sensor element 14 rises toward its activity temperature after the time t0. The element impedance Rt then gradually changes to a small value. However, the process for detecting the element impedance Rt cannot be performed while negative voltage application control is exercised (between the time t1 and time t3). Therefore, the value Rt is maintained at a value prevailing at the time t1 (FIG. 7D).

The device according to the present embodiment starts applying the positive voltage Vp1 to the sensor element 14 simultaneous with the internal-combustion engine starts up (FIG. 7A). The process for detecting the air-fuel ratio A/F is then continuously repeated in accordance with the sensor current (AD1 port output), further, the process for detecting the element impedance Rt is performed at predetermined intervals, until negative voltage application control begins at the time t1. If the sensor element 14 is sufficiently cool at the time of internal-combustion engine startup, virtually no sensor current is generated until the warm-up process for the sensor element 14 is adequately performed (FIG. 7B). Therefore, the air-fuel ratio A/F, which is calculated from the sensor current, is maintained at a virtually constant value for a certain period of time after the time t0 (FIG. 7C).

The microcomputer 34 judges that the temperature of the sensor element 14 reaches to the reaction start temperature (an appropriate value within the range of approximately 300 to 350° C.) when the element impedance Rt lowers a predefined reaction start judgment value. The "reaction start temperature" is a temperature at which the atmospheric-air-side electrode 22 and exhaust-side electrode 18 begin to perform their catalytic action, that is, a temperature at which desorption of the adsorbable species begins to be remarkable near the exhaust-side electrode 18. FIGS. 7A to 7G show a case where the above judgment is formulated at the time t1. At the time t1, the microcomputer 34 turns ON the negative voltage application control execution flag XAFVMCTL (FIG. 7F), and begins to exercise negative voltage application control.

When negative voltage application control begins, the voltage applied to the sensor element 14 is changed from the positive voltage Vp1 to the negative voltage Vm (FIG. 7A). More specifically, only switch circuit 60 is turned ON while switch circuits 50 and 52 are left OFF in the circuitry shown in FIG. 3. When the negative voltage Vm is applied to the sensor element 14, the oxygen ions taken in from the atmospheric-air-side electrode 22 move toward the exhaust-side electrode 18 and a negatively-oriented current (hereinafter referred to as the "negative current") flows through the sensor element 14. As mentioned earlier, the negative voltage Vm is set to a value that generates a sensor current whose absolute value is greater than when the positive voltage Vp1 is applied. Therefore, if the voltage applied to the sensor element 14 is changed to the negative voltage at the time t1, a sufficiently larger sensor current is then generated when compared to a period preceding the time t1 as indicated in FIG. 7B. In other words, a sufficiently large number of oxygen ions are conveyed toward the exhaust-side electrode 18 after the time t1.

If the sensor element 14 is further heated to a temperature of higher than the reaction start temperature (300 to 350° C.), a reducing substance is supplied to a location near the exhaust-side electrode 18 when the adsorbable species becomes desorbed. If, in such a situation, a large number of oxygen ions are conveyed toward the exhaust-side electrode 18, the generated reducing substance can be neutralized by the oxygen ions to inhibit the neighborhood of the exhaust-side electrode 18 from changing into a reduction atmosphere, and the generation of the reducing substance, that is, the desorption of the adsorbable species, can be urged. Therefore, if negative voltage application control is exercised at this stage as described earlier (see FIGS. 5 and 6), it is possible to minimize the extent of exhaust-air-fuel ratio rich displacement, which is caused by adsorbable species desorption, and reduce the period of time during which such displacement occurs.

The negative voltage Vm belongs to a region where the voltage applied to the sensor element 14 is proportional to the sensor current (see FIG. 4). Therefore, while negative voltage application control is being exercised, the element impedance can be detected, in principle, by viewing the ratio between the applied voltage and sensor current. It is hereinafter assumed that the element impedance detected during negative voltage application control is designated "Rm" and differentiated from the element impedance detected in the other situations, which is designated "Rt".

Immediately after the start of negative voltage application control, the sensor current corresponding to the sensor element impedance Rm and applied voltage Vm flows through the sensor element 14, and besides, movement of a charge due to the capacitance component of the sensor element 14 occurs. Therefore, an excessive sensor current flows in relation to the intrinsic element impedance Rm until the movement of the charge converges. If the element impedance Rm is calculated from such a sensor current, the resulting calculated element impedance Rm would be excessively low.

It is possible to predetermine the time required for the movement of the charge caused by the capacitance component of the sensor element 14 to converge. In FIGS. 7A to 7G, the period of time Tm1, which begins at the time t1, is the period of time required for the above convergence predetermined by means of adjustment work or the like. In the present embodiment, the microcomputer 34 inhibits the Rm calculation process during the time interval between the instant at which negative voltage application control begins and the instant at which the above period of time Tm1 elapses because it judges that the relationship between the sensor current and element impedance Rm is improper. When the period of time Tm1 elapses, the microcomputer 34 starts calculating the element impedance Rm in accordance with the voltage applied to the sensor element 14 (AD3-AD4) and the sensor current (AD2-AD3).

When the element impedance Rm decreases to a predefined termination judgment value, the microcomputer 34 concludes that the temperature of the sensor element 14 reaches to the termination judgment temperature (e.g., an appropriate value within the range of approximately 550 to 600° C.). The "termination judgment temperature" is a predefined temperature at which the adsorbable species, which is adsorbed around the exhaust-side electrode 18, is supposed to be completely desorbed. FIGS. 7A to 7G show a case where the above judgment is formulated at the time t2. When it is concluded that the temperature of the sensor element 14 reaches to the termination judgment temperature, the microcomputer 34 judges at that time point t2 that the benefit of applying a negative voltage to the sensor element 14 is gone, and changes the applied voltage to the sensor element 14 from the negative voltage Vm to the reverse current early convergence application voltage Vp2 (FIG. 7A). More specifically, the microcomputer 34 turns OFF switch circuit 60 and starts a process for driving switch circuit 50 in such a manner as to generate the reverse current early convergence application voltage Vp2. In the present embodiment, the reverse current early convergence application voltage Vp2 is generated by controlling switch circuit 50. However, an alternative is to furnish a switch for generating the reverse current early convergence application voltage Vp2 in addition to switch circuit 50 and use such an additional switch circuit to generate the reverse current early convergence application voltage Vp2.

Figure 8A:
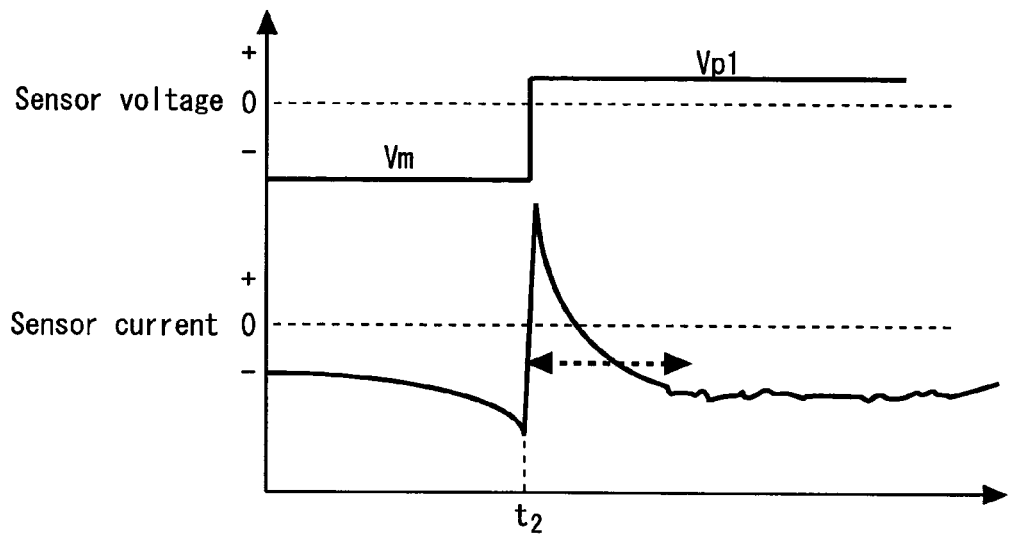
FIG. 8A is a timing diagram illustrating a phenomenon which occurs in a case where an applied voltage reverts to specific positive voltage Vp1 when necessity of application of negative voltage application is extinguished.
Figure 8B:
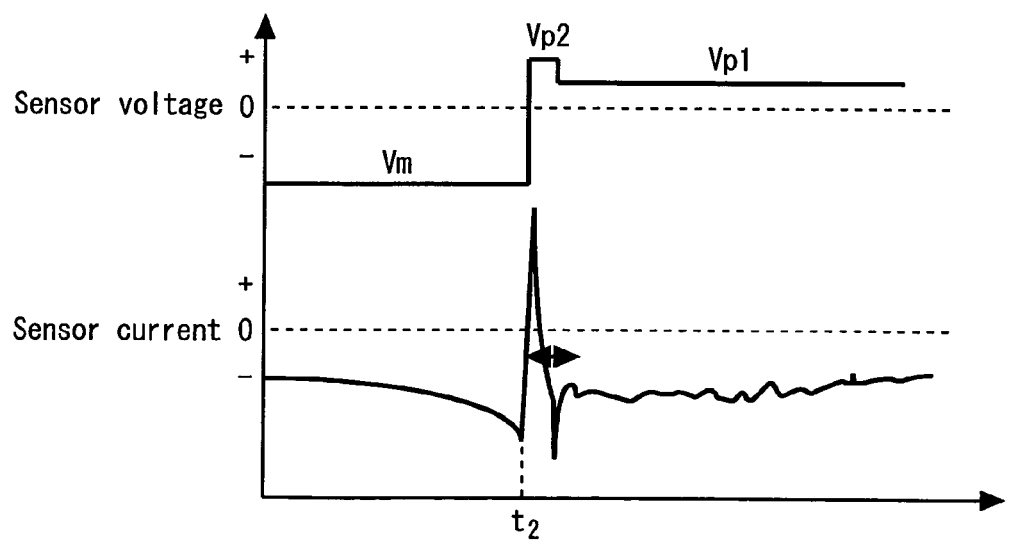
FIG. 8B is a timing diagram illustrating a phenomenon which occurs in a case where the applied voltage reverts to the positive voltage Vp1 via specific application voltage Vp2 for reverse current early convergence purpose.

FIGS. 8A and 8B are timing diagrams illustrating the reason why the microcomputer 34 changes the voltage applied to the sensor element 14 to the reverse current early convergence application voltage Vp2, which is higher than the positive voltage Vp1, at a time when necessity for applying the negative voltage disappear. More specifically, FIG. 8A is a timing diagram that illustrates a case where the applied voltage reverts to the positive voltage Vp1 at the time described above. On the other hand, FIG. 8B is a timing diagram that illustrates a case where the applied voltage temporarily changes to the reverse current early convergence application voltage Vp2 and then reverts to the positive voltage Vp1.

Immediately after the direction of the voltage applied to the sensor element 14 changes, movement of a charge occurs because of the capacitance component of the sensor element 14. Therefore, the sensor current value becomes a value determined by adding the above charge to the original current value during the time interval between the time t2 and the instant at which the movement of the charge terminates. The higher the voltage applied after voltage application direction reversal, the earlier the movement of the charge converges. Therefore, if the applied voltage is directly changed from the negative voltage Vm to the positive voltage Vp1 at the time t2, it takes a long period of time for the sensor current to revert to the normal value as indicated in FIG. 8A. If, on the other hand, the applied voltage is changed to the reverse current early convergence application voltage Vp2 and then restored to the positive voltage Vp1 after the time t2, the period of time required for the sensor current to revert to the normal value can be effectively reduced as indicated in FIG. 8B. Therefore, the present embodiment temporarily applies the reverse current early convergence application voltage Vp2 after negative voltage application is rendered unnecessary, and then restores the applied voltage to the positive voltage Vp1, as described earlier.

More specifically, the present embodiment maintains the reverse current early convergence application voltage Vp2 as the voltage applied to the sensor element 14 for a predetermined period Tp1 after the time t2, as shown in FIG. 8A. When the predetermined period Tp1 elapses, the applied voltage reverts to the positive voltage Vp1. Immediately after the applied voltage is changed from the reverse current early convergence application voltage Vp2 to the positive voltage Vp1, the sensor current is influenced by the capacitance component of the sensor element 14. The period Ta1, which follows the period Tp1 in FIGS. 7A to 7G is a predetermined period that is required for the influence to converge. The period Tp1 and the period Ta1 are predetermined as a combination that is supposed to be capable of minimizing the period of time required for restoring the sensor current to the normal value. When the period Ta1 elapses (time t3) after the applied voltage is changed to the positive voltage Vp1, the microcomputer 34 concludes that the sensor current has converged to the normal value, and turns OFF the negative voltage application control execution flag XAFVMCTL to terminate the negative voltage application control sequence.

As indicated in FIG. 7A, the absolute value of the reverse current early convergence application voltage Vp2 used in the present embodiment is smaller than that of the negative voltage Vm. When the voltage applied to an element having a capacitance component is to be changed for causing the influence of charge, which is caused by the capacitance component, to converge promptly, the absolute value of a voltage applied after reversal is usually made equal to that of a voltage applied before reversal. However, in the present embodiment, such applied voltage reversal is performed while the heater 26 is drove at a 100% duty ratio. In other words, the applied voltage is reversed in an environment in which the sensor element 14 is rapidly heated.

The higher the temperature of the sensor element 14, the higher the admittance of the sensor element 14. Therefore, the admittance of the sensor element 14 is greater when the reverse current early convergence application voltage Vp2 is applied (after the time t2) than when the negative voltage Vm is applied (before the time t2). The higher the admittance of the sensor element 14, the easier the charge transfer that is invoked by the capacitance component. Therefore, if the present embodiment uses the same absolute value for the negative voltage Vm and reverse current early convergence application voltage Vp2 when the applied voltage is changed from the negative voltage Vm to the reverse current early convergence application voltage Vp2, an excessive charge transfer is likely to occur. If, on the other hand, the absolute value of the reverse current early convergence application voltage Vp2 is smaller than that of the negative voltage Vm, such an excessive charge transfer is not likely to occur. As a result, a favorable situation can be created to let the sensor current revert to the normal value promptly. In this respect, the device according to the present embodiment has a favorable characteristic for reducing the time required for the air-fuel ratio sensor 10 to generate a normal output during the warm-up process.

It is conceivable for restore the negative voltage Vm to the positive voltage Vp1 to change the applied voltage after stopping the heating of the sensor element 14 so as to inhibit a change in its admittance. However, the movement of the charge, which is caused by the capacitance component of the sensor element 14, can readily converge within a short period of time if the sensor element 14 exhibits a high admittance. Therefore, the present embodiment continuously drives the heater 26 at a 100% duty ratio until the period Ta1 elapses after the applied voltage is set to the positive voltage Vp1 (till the time t3) as described earlier. In such a situation, the sensor element 14 is rapidly heated until the movement of the charge that should converge terminates. Therefore, a favorable condition is created for allowing the sensor output to converge to the normal value within a short period of time. In this respect, too, the device according to the present embodiment has a favorable characteristic for reducing the period of time during which the sensor output may shift.

The waveform indicated in FIG. 7E represents the integrated value ΣIm of the sensor current (negative current Im) that is generated in a situation where the negative voltage Vm is applied to the sensor element 14. Since the negative current Im is defined as a value having a negative sign, the integrated value ΣIm of the negative current Im is indicated in a negative region. The integrated value ΣIm correlates with the number of oxygen ions that are pumped toward the exhaust-side electrode 18 due to execution of negative voltage application control. Further, the number of oxygen ions correlates with the progress of adsorbable species desorption. Therefore, the microcomputer 34 may calculate the integrated value ΣIm of the negative current Im as indicated by FIG. 7E, and stop applying the negative voltage when the integrated value ΣIm reaches a predetermined termination judgment value.

[Detailed Description of Processing Steps Performed by the Control Device]

Figure 9:
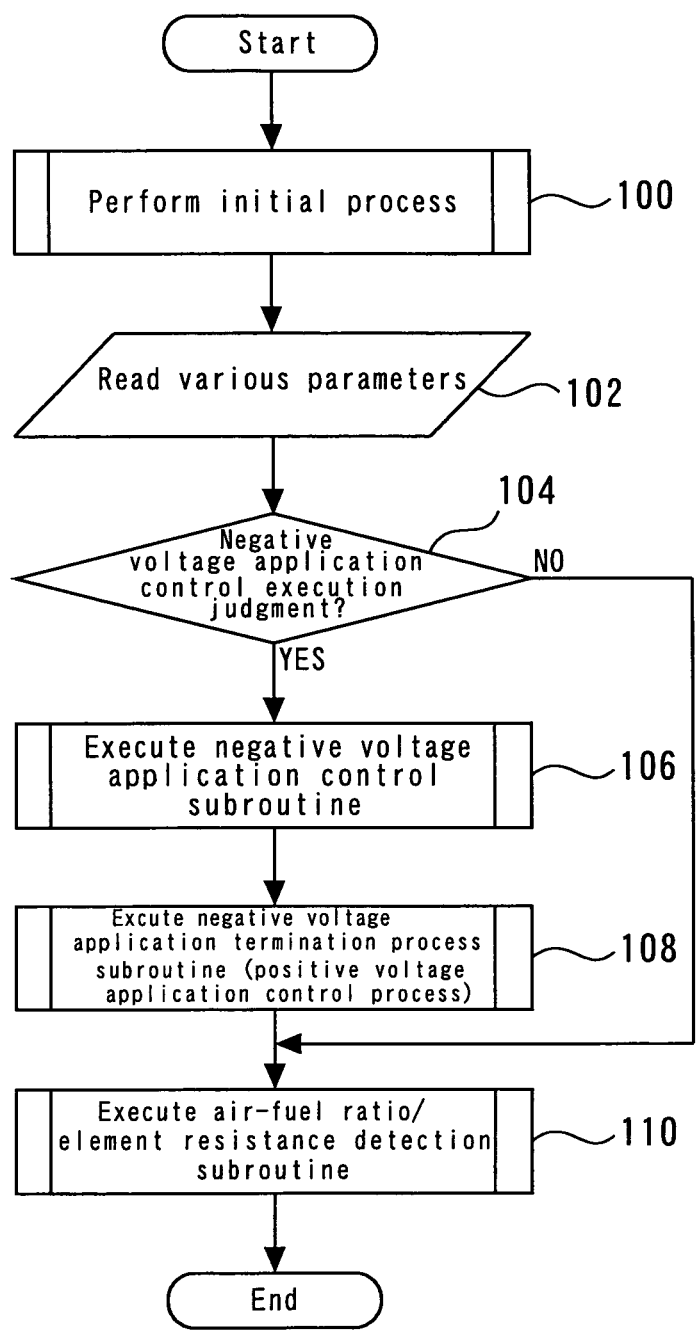
FIG. 9 is a flowchart illustrating flow of processing steps that are performed for controlling the sensor element of the air-fuel ratio sensor of the first embodiment.

The processing steps that the control device according the present embodiment performs in relation to the sensor element 14 will now be described in detail with reference to FIGS. 9 through 12. FIG. 9 is a flowchart illustrating the overall flow of the processing steps that are performed for the sensor element 14. The routine shown in FIG. 9 is executed each time the internal-combustion engine is started.

In the routine shown in FIG. 9, there are performed first a predetermined initial process (step 100) and various parameter reads (step 102). After completion of these steps, a negative voltage application control execution query step is performed (step 104). More specifically, the negative voltage application control execution query step is performed to judge whether the conditions are established for excusing the negative voltage application control in addition to the process for detecting the air-fuel ratio A/F and element impedance Rt. This processing step will be described in detail later with reference to FIG. 10.

If query step 104, which is mentioned above, is answered "No", the program flow skips steps 106 and 108, which exercise negative voltage application control, and immediately performs processing step 110. If, on the other hand, query step 104 is answered "Yes", the program flow proceeds to execute a negative voltage application control subroutine (step 106). The negative voltage application control subroutine applies the negative voltage Vm to the sensor element 14 for an appropriate period of time. In other words, this subroutine completes a process that is to be performed during a period between the time t1 and time t2 as indicated in FIGS. 7A to 7G. The contents of this subroutine will be described in detail later with reference to FIG. 11.

After termination of the negative voltage application control subroutine, step 108 is performed to execute a negative voltage application termination process subroutine. This subroutine terminates the application of the negative voltage Vm to the sensor element 14 and uses the restoration application voltage Vp2 as the applied voltage for an appropriate period of time. In other words, the subroutine completes a process that is to be performed during a period between the time t2 and time t3 as indicated in FIGS. 7A to 7G. The contents of this subroutine will be described in detail later with reference to FIG. 12.

After termination of the negative voltage application termination process subroutine, step 110 is performed to execute an air-fuel ratio/element resistance detection subroutine. This subroutine performs a process for detecting the air-fuel ratio A/F in accordance with the sensor current while applying the positive voltage Vp1 to the sensor element and performs a process for detecting the element impedance Rt while alternating the applied voltage between an impedance measurement positive voltage and impedance measurement negative voltage at predetermined intervals. The contents of this subroutine are not described in detail herein because they are the same as disclosed, for instance, by Japanese Patent Laid-open No. Hei 9-292364.

Figure 10:
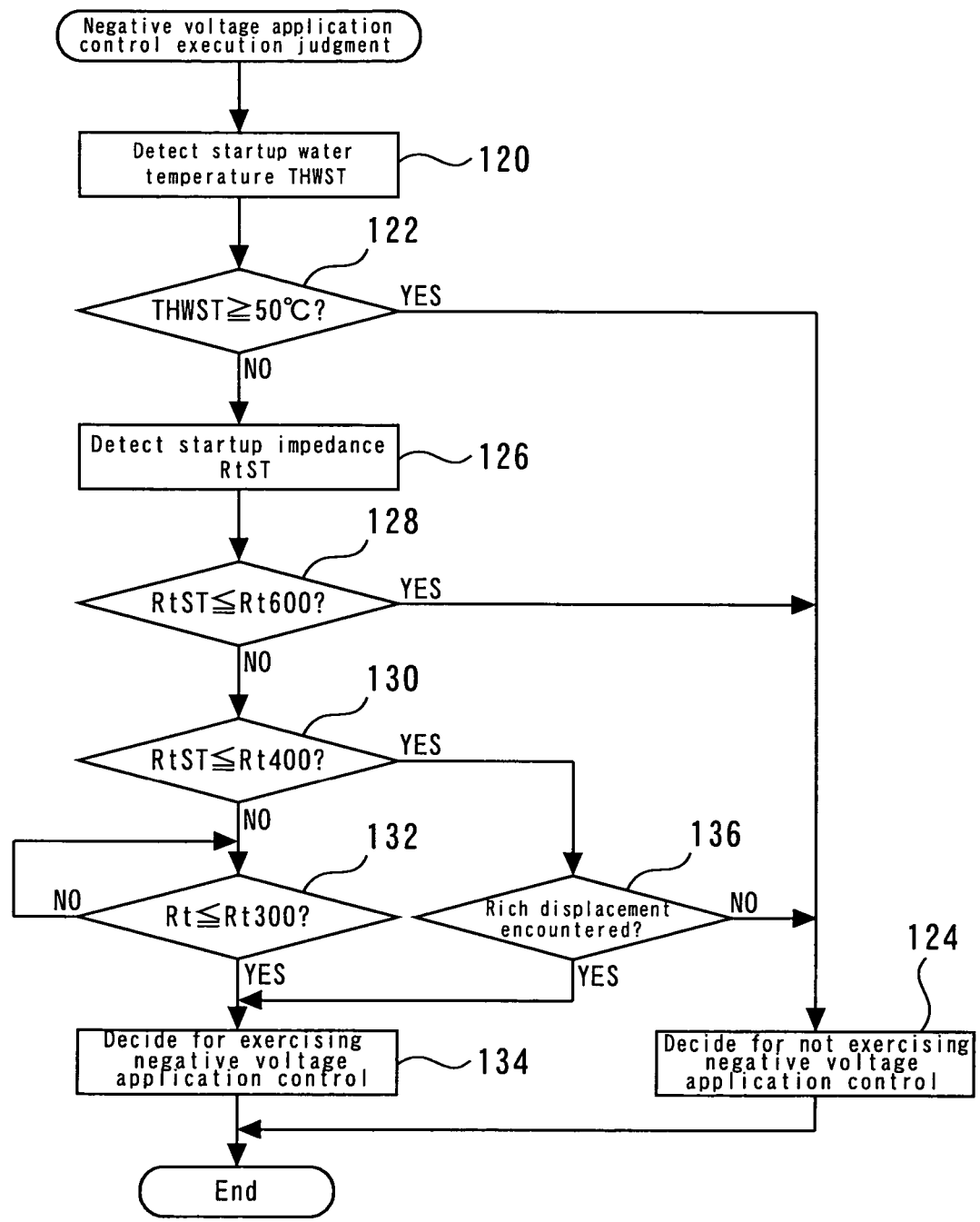
FIG. 10 is a flowchart illustrating a series of processing sequences that are performed as negative voltage application control execution judgment in the routine shown in FIG. 9.

FIG. 10 is a flowchart illustrating a series of processing sequences that are followed in step 104 above for negative voltage application control execution judgment. While the routine shown in this flowchart is being executed, the same subroutine that is executed in step 110 above is executed as well. As a result, the process for detecting the air-fuel ratio A/F and element impedance Rt is repeatedly executed.

The routine shown in FIG. 10 first performs step 120 to detect a cooling water temperature THWST at internal-combustion engine startup. Next, step 122 is performed to judge whether the startup water temperature THWST is 50° C. (predetermined warm-up judgment temperature) or higher. If THWST≥50° C., it can be concluded that the internal-combustion engine stop period is short, and that the sensor element 14 is not sufficiently cooled yet. While the internal-combustion engine is cooled after its stop, the adsorbable species is adsorbed by the sensor element 14. Consequently, if the sensor element 14 is still maintained at a high temperature, it can be concluded that the adsorbable species is not adsorbed, and that there is no need to exercise negative voltage application control for the purpose of counteracting the influence of the adsorbable species. In such an instance, therefore, step 124 is immediately followed so as not to exercise negative voltage application control. If step 124 is performed so as not to exercise negative voltage application control, the routine shown in FIG. 9 skips steps 106 and 108, which provide negative voltage application control, and then immediately executes the air-fuel ratio/element resistance detection subroutine.

If the result of step 122 in the routine shown in FIG. 10 indicates that the startup water temperature THAST is not the warm-up judgment temperature or higher, step 126 is performed to detect the sensor element's startup element impedance RtST, which prevails at startup. Further, step 128 is performed to judge whether the detected startup impedance RtST is equal to the adsorbable species adsorption value Rt600 or lower. The adsorbable species adsorption value Rt600 is an element impedance Rt that is attained when the temperature of the sensor element 14 coincides with the "adsorbable species adsorption temperature". The adsorbable species adsorption temperature is an upper-limit temperature (600° C. in the present embodiment) at which the sensor element 14 may begin to adsorb the adsorbable species during a cooling process for the sensor element 14.

If it is found in step 128 that RtST≤Rt600, it can be concluded that the temperature of the sensor element 14 is higher than the adsorbable species adsorption temperature (600° C.), and that adsorbable species adsorption has not possibly started. In such an instance, negative voltage application control need not be exercised. Therefore, step 124 is immediately followed so as not to exercise negative voltage application control. If, on the other hand, it is found in step 128 that the startup impedance RtST is higher than the adsorbable species adsorption value Rt600, step 130 is performed to judge whether the value RtST is equal to or smaller than the adsorbable species judgment value Rt400. The adsorbable species judgment value Rt400 represents an element impedance Rt that is attained when the temperature of the sensor element 14 coincides with an "adsorbable species judgment temperature". The adsorbable species judgment temperature is a lower-limit temperature (400° C. in the present embodiment) at which adsorbable species adsorption may not take place during a cooling process for the sensor element 14.

If it is found in step 128 that RtST is not equal to or less than Rt400, it can be concluded that the temperature of the sensor element 14 is lower than the adsorbable species judgment temperature. In other words, it can be concluded that the adsorbable species is adsorbed by the sensor element 14. In this instance, step 132 is then performed to judge whether the current element impedance Rt is below the reaction start judgment value Rt300, that is, to judge whether the conditions for starting negative voltage application control are established. If it is found that Rt≤Rt300, it is concluded that temperature of the sensor element 14 reached to the reaction start temperature (an appropriate value within the range of 300 to 350° C.). It is therefore determined that negative voltage application control is to be exercised (step 134). When step 134 is performed for exercising the control, step 106, which is shown in FIG. 9, is followed to start the negative voltage application control subroutine.

If it is found in step 130 that RtST is equal to or less than Rt400, step 136 is then performed to apply the positive voltage Vp1 to the sensor element 14 and to judge whether the output of the sensor element 14 is affected by rich displacement. If it is judged that no rich displacement is found in the output, step 124 is then performed. On the other hand, if it is determined that rich displacement is found in the output, step 134 is exercised to excuse negative voltage application control.

As described above, the routine shown in FIG. 10 decides to exercise negative voltage application control only when the influence of the adsorbable species is superposed over the output of the air-fuel ratio sensor 10 at internal-combustion engine restart. Further, the decision for exercising the control can be made only for a period that is effective for curbing the influence. Therefore, the device according to the present embodiment can effectively prevent the negative voltage Vm from being applied wastefully.

Figure 11:
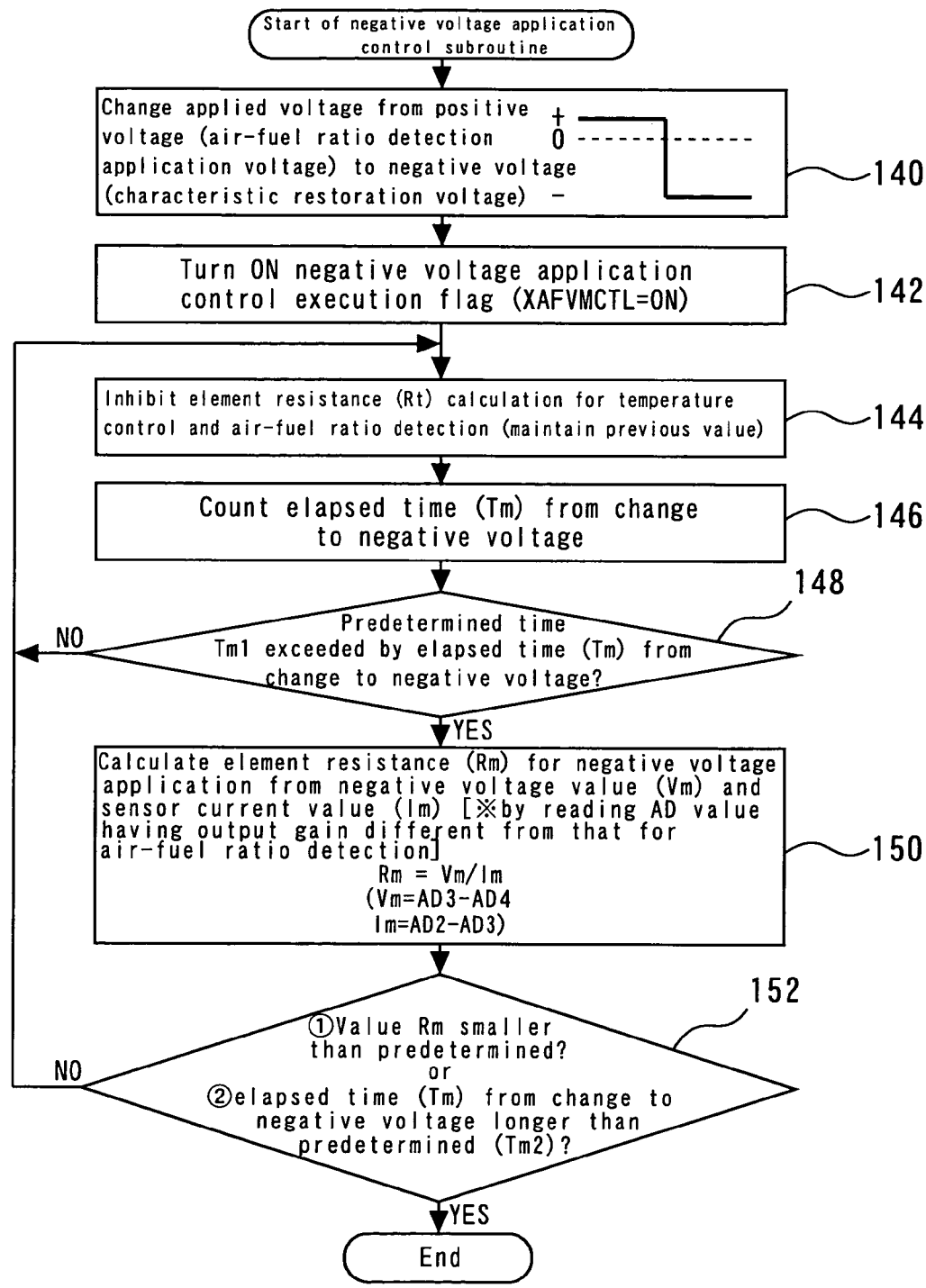
FIG. 11 is a flowchart illustrating a series of processing sequences that are performed as a subroutine for negative voltage application control in the routine shown in FIG. 9.

FIG. 11 is a flowchart illustrating the details of the negative voltage application control subroutine that is executed in step 106 above. This subroutine first changes the voltage application to the sensor element 14 from the positive voltage Vp1 to the negative voltage Vm (step 140). Next, step 142 is performed to turn ON the negative voltage application control execution flag XAFVMCTL for the purpose of indicating that negative voltage application control has started.

Next, step 144 is performed to inhibit the calculation of the element impedance Rt which is the basis of temperature control of the heater 26 and inhibit the detection of the air-fuel ratio A/F which is based on the sensor current. The element impedance Rt and air-fuel ratio A/F are then fixed at values prevailing at the beginning of negative voltage application control until negative voltage application control terminates (see a period between the time t1 and time t3 in FIGS. 7C and 7D). Next, step 146 is performed to count the elapsed time Tm which denotes the elapse time after the start of negative voltage application control. Step 148 is then performed to judge whether a predetermined period of time Tm1 is reached by the elapsed time Tm.

As mentioned earlier, the predetermined period of time Tm1 is the time interval between the instant at which the voltage application to the sensor element 14 changes from the positive voltage Vp1 to the negative voltage Vm and the instant at which the movement of the charge caused by the capacitance component of the sensor element 14 converges (see FIG. 7B). If the above judgment sequence concludes that Tm is not equal to or greater than Tm1, it is judged that the sensor current Im is not stabilized at a value corresponding to the element impedance Rm prevailing upon negative voltage application. Processing step 144 is then performed again. If, on the other hand, it is found that Tm≥Tm1, the element impedance Rm prevailing upon negative voltage application is calculated as follows by dividing the negative voltage Vm by the negative current Im (step 150):

$$Rm = Vm/Im \quad (1)$$

The negative voltage Vm is a voltage that is actually developed across the sensor element 14. More specifically, it is obtained by subtracting the AD4 port potential from the AD3 port potential within the circuit shown in FIG. 3. The negative current Im is a sensor current that is generated due to the application of the negative voltage Vm. In the present embodiment, the value of the negative current Im is obtained by subtracting the AD3 port potential from the AD2 port potential.

The routine shown in FIG. 11 judges whether the element impedance Rm calculated in processing step 150 is below the termination judgment value and judges whether a predetermined period of time Tm2 is reached by the elapsed time Tm after the start of negative voltage application control (step 152). If the former condition is met, it can be concluded that the sensor element 14 is heated to a temperature above the termination judgment temperature (approximately 550 to 600° C.). If, on the other hand, the latter condition is met, it can be concluded that negative voltage application control has been exercised for a period of time required for thorough adsorbable species desorption. If neither of these conditions is met, the microcomputer 34 judges that the time for terminating the application of the negative voltage Vm has not come yet, and repeats processing steps 144 and beyond. On the other hand, if at least one of these conditions is met, the microcomputer 34 judges that the time for terminating the application of the negative voltage Vm has come, and terminates the routine. When the routine shown in FIG. 11 terminates, the program flow proceeds to perform processing step 108 shown in FIG. 9, that is, the negative voltage application termination process subroutine.

As described above, the routine shown in FIG. 11 can apply the negative voltage Vm to the sensor element 14 while adsorbable species desorption is anticipated during the warm-up process for the sensor element 14. Therefore, the device according to the present embodiment can efficiently achieve adsorbable species desorption during the warm-up process for the sensor element 14 and effectively reduce the period during which the output of the sensor element 14 may be affected by rich displacement due to the influence of the adsorbable species.

Figure 12:
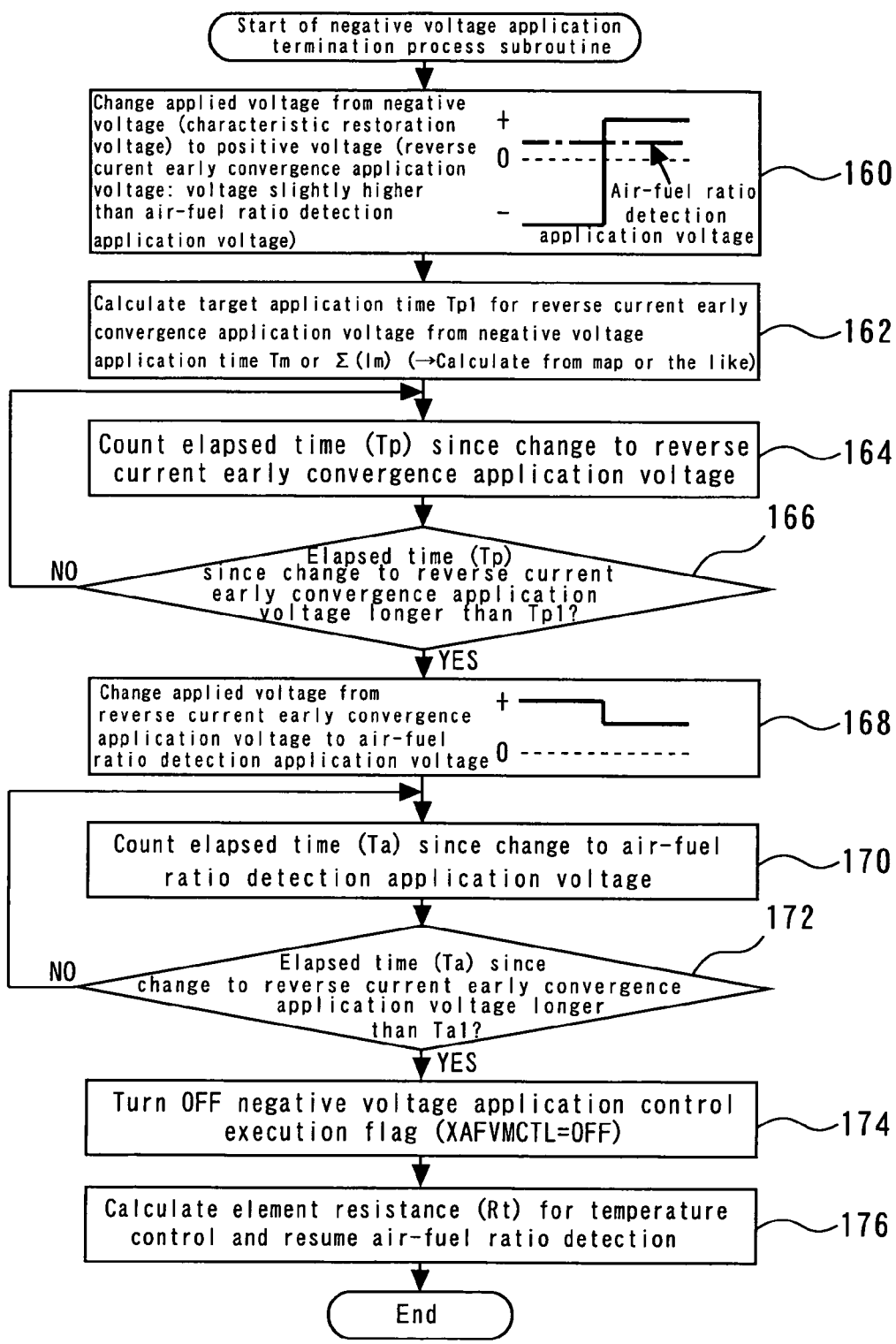
FIG. 12 is a flowchart illustrating a series of processing sequences that are performed as a subroutine for negative voltage application termination process in the routine shown in FIG. 9.

FIG. 12 is a flowchart illustrating the details of the negative voltage application termination process subroutine that is executed in step 108 above. This subroutine first changes the voltage application to the sensor element 14 from the negative voltage Vm to the reverse current early convergence application voltage Vp2 (step 160). As described earlier, the reverse current early convergence application voltage Vp2 is greater by a predetermined value than the positive voltage Vp1 to which the applied voltage should eventually converge.

Next, step 162 is performed to calculate a target application time Tp1 for the reverse current early convergence application voltage Vp2 in accordance with the negative voltage application time Tm or the integrated value ΣIm of the negative current Im. The reverse current early convergence application voltage Vp2 is applied at the end time of the application of the negative voltage Vp1 for purpose of promptly terminating the charge movement caused by the capacitance component of the sensor element 14. The longer the application period for the negative voltage Vp1 and the larger the amount of the negative current Im that flows during the application period, the greater the amount of the charge movement to be terminated. In step 162, therefore, the longer the negative voltage application time Tm or the greater the integrated value ΣIm, the longer the setting for the target application time Tp1 for the reverse current early convergence application voltage Vp2. The device according to the present embodiment memorizes a map that defines the value Tp1 in relation to the values Tm or ΣIm. The value Tp1 is calculated herein by referring to the map.

Next, step 164 is performed to count the elapsed time Tp that is an elapse time after the applied voltage change from the negative voltage Vm to the reverse current early convergence application voltage Vp2. Next, step 166 is performed to judge whether the elapsed time Tp is longer than the target application time Tp1. If it is found in step 166 that Tp is not equal to or greater than Tp1, processing step 164 is repeated. If, on the other hand, it is found that Tp≥Tp1, step 168 is performed to change the applied voltage to the sensor element 14 from the reverse current early convergence application voltage Vp2 to the positive voltage Vp1.

When the application of the positive voltage Vp1 begins, step 170 is followed to start counting the elapse time Ta after the start of such voltage application. When the elapse time Ta exceeds the time Ta1 required for sensor current stabilization (step 172), the negative voltage application control execution flag XAFVMCTL turns OFF (step 174). After an instruction is issued for resuming the sequence for calculating the element impedance Rt and detecting the air-fuel ratio A/F (step 176), the routine terminates. When the routine shown in FIG. 12 terminates, processing step 110, which is shown in FIG. 9, is performed to start the air-fuel ratio/element impedance detection subroutine.

As described above, the routine shown in FIG. 12 can cause the sensor current to promptly converge to a value corresponding to the positive voltage Vp1 by means of continuously keeping the applied voltage to the restoration positive voltage Vp2 for an appropriate period after the application of the negative voltage Vm to the sensor element 14 is stopped. Further, the routine can inhibit the resumption of a sequence for calculating the element resistance Rt and detecting the air-fuel ratio A/F until a predetermined period of time Ta1 elapses after an applied voltage change to the positive voltage Vp1. Therefore, the device according to the present embodiment can achieve sensor characteristic restoration within a minimum period of time after the end of the application of the negative voltage Vm to the sensor element 14, and resume a sequence for accurate air-fuel ratio detection after the minimum period has elapsed.

Figure 13:
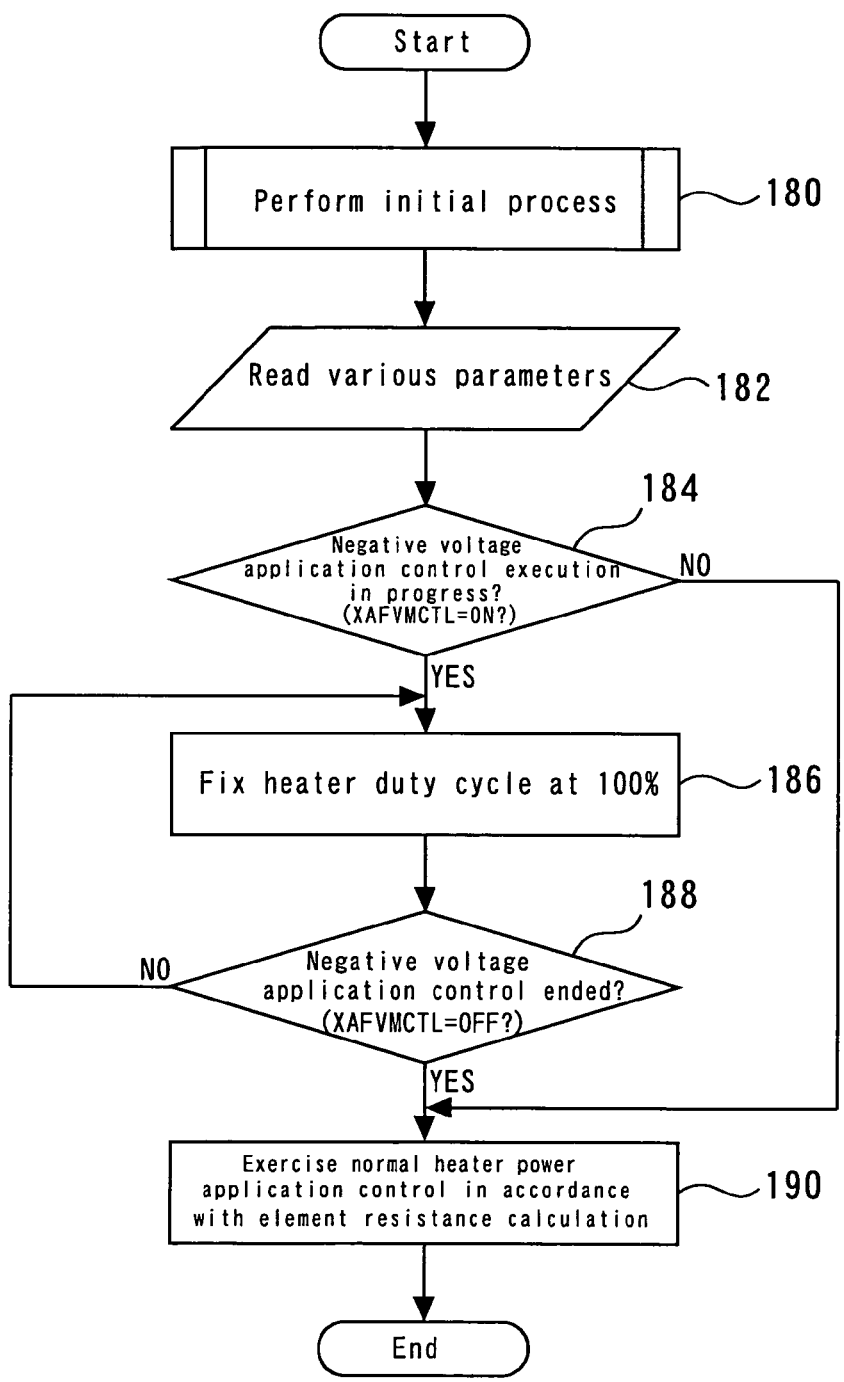
FIG. 13 is a flowchart illustrating flow of processing steps that are performed for controlling a heater of the air-fuel ratio sensor of the first embodiment.

The above routines, which have been described with reference to FIGS. 9 through 12, are the routines that the device according to the present embodiment executes in relation to the sensor element 14. The device according to the present embodiment executes a routine for controlling the heater 26 in addition to the above routines. FIG. 13 is a flowchart illustrating a routine that is executed for heater control in the present embodiment. This routine is initiated upon each internal-combustion engine startup as is the case with the routine shown in FIG. 9.

The routine shown in FIG. 13 first performs a predetermined initial process (step 180) and various parameter reads (step 182). After completion of these processing steps, a negative voltage application control execution query step is performed (step 184). More specifically, step 184 is performed to judge whether the negative voltage application control execution flag XAFVMCTL is ON. If it is found in step 184 that negative voltage application control is being exercised, step 186 is followed to perform a process for fixing the drive duty ratio for the heater 26 at 100%. The drive duty ratio is then maintained at 100% until it is found that negative voltage application control is ended or it is judged that the negative voltage application control judgment flag XAFVMCTL is OFF (step 188).

If it is found in step 188 that negative voltage application control is ended or if it is found in step 184 that the flag XAFVMCTL is not ON, normal heater power application control is exercised (step 190). The term "normal heater power application control" refers to a process in which the heater 26 is driven at an appropriate duty ratio in order to ensure that the temperature of the sensor element 14 coincides with the target temperature. More specifically, there are performed in step 190 a process for detecting the element impedance Rt, a process for determining the difference ΔRt between the detected impedance value Rt and the target impedance Rtgt, a process for calculating the drive duty ratio of the heater 26 in accordance with the determined difference ΔRt, and a process for driving the heater 26 at the calculated drive duty ratio.

According to the process described above, it is possible to drive the heater 26 in its full capacity after the application of the negative voltage Vm starts, until the time Ta1 required for sensor current stabilization elapses after the applied voltage is changed to the positive voltage Vp1, thereby rapidly warming up the sensor element 14. The higher the admittance exhibited by the sensor element 14, that is, the higher the temperature of the sensor element 14, the shorter the period of time within which the charge movement caused by the capacitance component of the sensor element 14 converges. Therefore, the above method for driving the heater 26 is an optimum method for minimizing the time required for a charge movement in a process in which the applied voltage sequentially changes from the negative voltage Vm through the reverse current early convergence application voltage Vp2 to the positive voltage Vp1. Consequently, the device according to the present embodiment sufficiently reduces the period during which an error is superposed over the sensor output within the warm-up process for the sensor element 14.

As described above, the device according to the present embodiment sufficiently reduces the period of time during which the influence of the adsorbable species is superposed over the sensor output within the warm-up process by :a) changing the applied voltage to the negative voltage Vm during the warm-up process; b) applying the reverse current early convergence application voltage Vp2 after negative voltage application; c) permitting the air-fuel ratio A/F to be detected in a predetermined period of time Ta1 after the applied voltage is restored to the positive voltage Vp1; and d) driving the heater 26 at a 100% duty ratio until the elapse of the predetermined period of time Ta1 is recognized. As a result, the device according to the present embodiment creates, within a sufficiently short period of time after internal-combustion engine startup, a state where the output of the air-fuel ratio sensor 10 is reliable.

Figure 14:
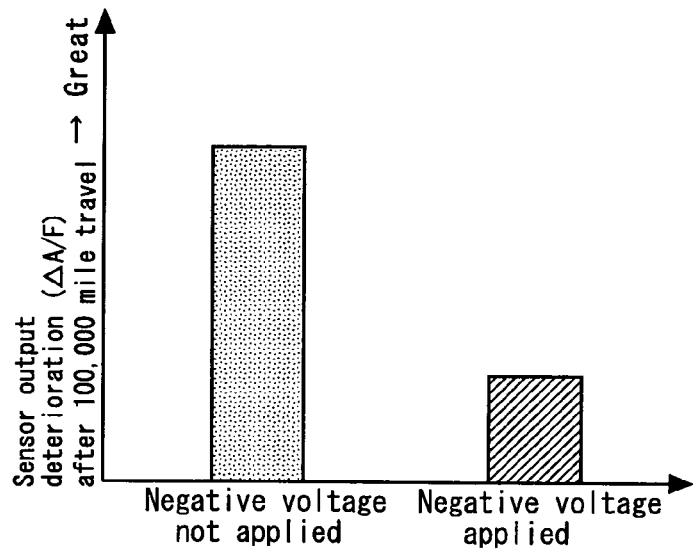
FIG. 14 relates to a sensor output deterioration prevailing, and shows comparison result between a case where negative voltage is applied and a case where the negative voltage is not applied.

In addition to the advantages described above, the device according to the present embodiment enhances the durability of the air-fuel ratio sensor 10. FIG. 14 illustrates such an additional advantage. More specifically, FIG. 14 relates to the sensor output deterioration prevailing when a cumulative traveled distance of 100,000 km is reached, and makes a sensor output deterioration comparison between a case where negative voltage application control is not exercised (left-hand side of the figure) and a case where negative voltage application control is exercised (right-hand side of the figure). As indicated in the figure, the output deterioration of the air-fuel ratio sensor 10 is significantly smaller when negative voltage application control is exercised than when negative voltage application control is not exercised. As described above, the device according to the present embodiment can stabilize the output characteristic of the air-fuel ratio sensor 10 for a long period of time.

In the first embodiment, which has been described above, the control target is limited to the air-fuel ratio sensor 10. However, the present invention may alternatively control an oxygen sensor that greatly varies its output depending on whether the exhaust air-fuel ratio is rich or lean.

In the first embodiment, which has been described above, negative voltage application control does not begin until the execution conditions for negative voltage application control are established after internal-combustion engine startup (see step 104 above and FIG. 10). However, an alternative method may be employed for the start of negative voltage application control. More specifically, negative voltage application control may always be started immediately after internal-combustion engine startup without having to wait until the execution conditions are established.

In a situation where the internal-combustion engine is cold-started, the first embodiment, which has been described above, concludes that the reaction start temperature is exceeded by the sensor element 14 when the element impedance Rt falls below the reaction start judgment value, then beginning to exercise negative voltage application control. However, the instruction for the start of negative voltage application control may be issued at an alternative time. For example, the instruction for the start of negative voltage application control subsequent to a cold start may be issued when a predetermined period of time elapses after internal-combustion engine startup, when a predetermined exhaust temperature is reached, or when a predetermined cumulative amount of power application to the heater 26 is reached.

The first embodiment, which has been described above, checks the element impedance Rm to judge whether the application of the negative voltage Vm should terminate (see step 152 above). However, such a judgment may be formulated in an alternative manner. More specifically, the integrated value $\Sigma$Im of the negative current Im, that is, the integrated value $\Sigma$Im of the sensor current Im generated after the start of the application of the negative voltage Vm may be checked to judge whether the application of the negative voltage Vm should terminate.

The first embodiment, which has been described above, drives the heater 26 at a 100% duty ratio before negative voltage application control terminates. However, an alternative heater drive method may be used. More specifically, the intended purpose is achieved when the heater 26 is subjected to open control in such a manner that the sensor element 14 is rapidly heated. A smaller duty ratio may be used as far as the above conditions are met.

In the first embodiment, which has been described above, switch circuits 50, 52, and 60 are turned ON or OFF to change the voltage applied to the sensor element 14. However, the applied voltage may be changed in an alternative manner. More specifically, the voltage applied to the sensor element 14 may be changed by preparing a sensor element control circuit 28, which is capable of varying the application voltage in accordance with an input value to the D/A converter, and allowing the microcomputer 34 to vary the signal to be supplied to the D/A converter.

Figure 15:
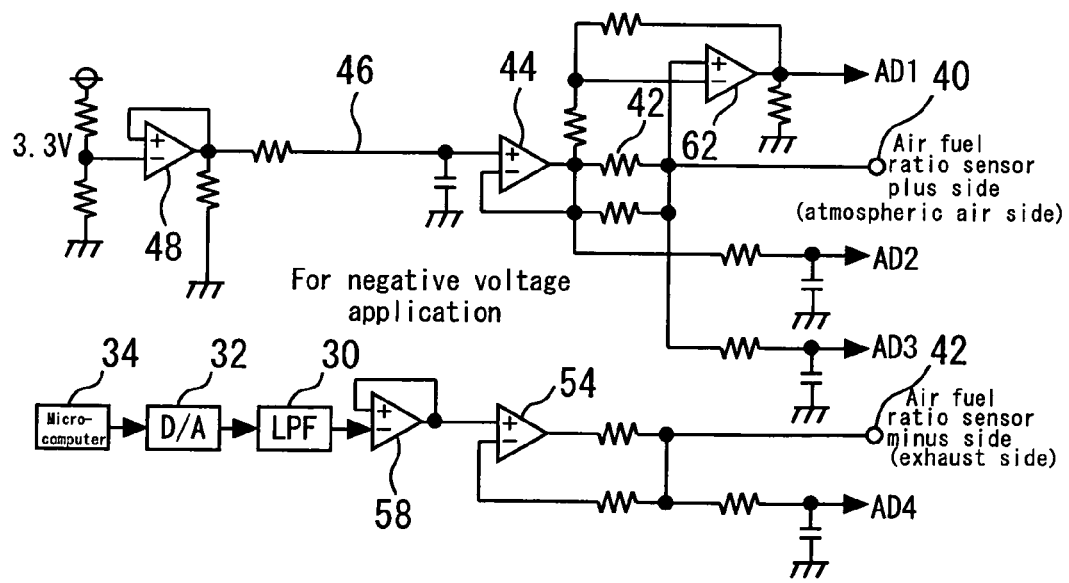
FIG. 15 is a circuit diagram that shows another example of sensor element control circuit being usable in the control device of the first embodiment.

FIG. 15 is a circuit diagram that shows an example of the sensor element control circuit 28 having the function described above. The sensor element control circuit 28 shown in FIG. 15 is the same as the circuit shown in FIG. 3 except that switch circuits 50, 52, and 60 excluded, and that the input into buffer circuit 58 is replaced by a signal passing through the LPF 30 (see FIG. 2). The components shown in FIG. 15 and in FIG. 2 or 3 are designated by the same reference numerals when they are identical with each other. The circuit shown in FIG. 15 properly changes the voltage applied to the sensor element 14 by appropriately varying an instruction signal that is generated from the microcomputer 34. In this manner, the circuit shown in FIG. 15 implements the same functionality that is implemented by the circuit shown in FIG. 3.

The major benefits of the present invention described above are summarized as follows:

According to a first aspect of the present invention, a negative voltage can be applied to the sensor element during a sensor element warm-up process. When a negative voltage is applied to the sensor element during the warm-up process, the influence of the adsorbable species, which becomes desorbed during the sensor element warm-up process, can be offset early. This makes it possible to decrease the period of time during which the influence of the adsorbable species is superposed over the sensor output. As a result, the present invention contributes to reducing the time interval between the instant at which the internal-combustion engine starts up and the instant at which the exhaust gas sensor output stabilizes.

According to a second aspect of the present invention, it is possible to properly prevent the solid electrolyte layer from being blackened upon negative voltage application.

According to a third aspect of the present invention, it is possible to ensure that negative voltage application does not start before the sensor element reaches its reaction start temperature. The adsorbable species does not begin to become desorbed until the sensor element reaches its reaction start temperature. Therefore, the period of time during which the influence of desorption persists does not decrease much even when a negative voltage is applied before the sensor element reaches its reaction start temperature. The present invention prevents the negative voltage from being applied wastefully during such a period.

According to a fourth aspect of the present invention, it is possible to prevent the negative voltage from being continuously applied after the sensor element reaches its termination judgment temperature. The influence of adsorbable species desorption disappears by the time the sensor element reaches its termination judgment temperature. The present invention prevents the negative voltage from being applied wastefully after such an influence disappears.

According to a fifth aspect of the present invention, it is possible to prevent the negative voltage from being continuously applied after the integrated sensor current value reaches the termination judgment value, which occurs after the sensor element reaches its predefined reaction start temperature. The influence of adsorbable species desorption disappears by the time the integrated sensor current value reaches the termination judgment value. The present invention prevents the negative voltage from being applied wastefully after such an influence disappears.

According to a sixth aspect of the present invention, a reverse current early convergence application voltage, which is greater than the positive voltage, can be applied to the sensor element for a predetermined period of time after the end of negative voltage application. Immediately after the direction of the applied voltage reverses, an overcurrent arising out of the sensor element's capacitance component flows. The present invention reduces the period of time during which the overcurrent flows and properly decreases the time required for the sensor current to converge to its stable value.

According to a seventh aspect of the present invention, it is possible to inhibit the negative voltage from being applied if the sensor element temperature remains above the adsorbable species adsorption temperature at the beginning of sensor element warm-up. Adsorbable species are adsorbed by the sensor element when its temperature lowers. Therefore, if the sensor element temperature is maintained above the adsorbable species adsorption temperature at the beginning of warm-up, it can be judged that the adsorbable species will not be adsorbed by the sensor element. The present invention prevents the negative voltage from being applied wastefully under such circumstances.

According to an eighth aspect of the present invention, it is judged whether the sensor output suffers rich displacement if the sensor element temperature is maintained above the adsorbable species judgment temperature at the beginning of sensor element warm-up. If it is judged that no such rich displacement is encountered, negative voltage application can be inhibited. If the sensor element temperature is higher than the adsorbable species judgment temperature at the beginning of warm-up, it can be judged that there is possibility that no adsorbable species is adsorbed by the sensor element. If the sensor output does not suffer from rich displacement in such an instance, it can be concluded that the adsorbable species is not adsorbed by the sensor element. The present invention prevents the negative voltage from being applied wastefully under circumstances where such a conclusion can be formed.

According to a ninth aspect of the present invention, predefined electrical power can be supplied to the heater using open control for a period of time during which the negative voltage or reverse current early convergence application voltage is applied to the sensor element for sensor element warm-up. Therefore, the present invention ensures that sensor element heating properly continues during the above period of time.

According to a tenth aspect of the present invention, the sensor current flowing upon negative voltage application can be acquired at a smaller gain than when the sensor current flowing upon positive voltage application is acquired. When the negative voltage is applied, a sufficiently larger sensor current arises than when the positive voltage is applied. The present invention acquires each sensor current at an appropriate gain, thereby making it possible to achieve sensor current acquisition with high accuracy under any circumstances.

Further, the present invention is not limited to these embodiments, but variations and modifications may be made without departing from the scope of the present invention. The entire disclosure of Japanese Patent Application No. 2003-285816 filed on Aug. 4, 2003 including specification, claims, drawings and summary are incorporated herein by reference in its entirety.

The invention claimed is:

1. A control device for an exhaust gas sensor that is to be mounted in an exhaust path of an internal-combustion engine, wherein said exhaust gas sensor is equipped with a sensor element having a function for pumping oxygen in a gas, the control device comprising:
a positive voltage applicator that applies a positive voltage to said sensor element;
a sensor current detector that detects a sensor current flow through said sensor element;
a heater that heats said sensor element;
a negative voltage applicator that applies a negative voltage, which is a reversal of said position voltage, to said sensor element; and
a microcomputer having control logic that causes the microcomputer to:
acquire a sensor current flow prevailing upon application of said positive voltage as a sensor output;
heat said sensor element by driving said heater after internal-combustion engine startup; and
apply a negative voltage when a temperature of said sensor element reaches a predetermined reaction start temperature within a rune between 300° C. and 350° C. and terminates the application of said negative voltage when the temperature of said sensor element reaches a termination judgment temperature which is previously determined to be lower than the activation temperature of said sensor element within a range between 550° C. and 600° C. as a temperature at which said adsorbable species is completely desorbed, after internal-combustion engine startup said microcomputer applies the negative voltage to said sensor element continuously during an entire time period in which the temperature of said sensor element is in a range of 350 to 550° C., during the initial warm-up process for said sensor element.

2. The control device for an exhaust gas sensor of an internal-combustion engine according to claim 1, wherein
said sensor element includes a solid electrolyte layer, and the value of said negative voltage is set so as not to invoke blackening of said solid electrolyte layer.

3. The control device for an exhaust gas sensor of an internal-combustion engine according to claim 1, wherein the microcomputer:
acquires the temperature of said sensor element; and
whether the temperature of said sensor element reaches said reaction start temperature is judged based on the temperature acquired by the microcomputer.

4. The control device for an exhaust gas sensor of an internal-combustion engine according to claim 1, wherein the microcomputer:
acquires the temperature of said sensor element; and
whether the temperature of said sensor element reaches said termination judgment temperature is judged based on the temperature acquired by the microcomputer.

5. The control device for an exhaust gas sensor of an internal-combustion engine according to claim 1, wherein the microcomputer:
calculates the integrated value of a sensor current generated since the temperature of the sensor element reaches said reaction start temperature; and
whether the temperature of said sensor element reaches said reaction start temperature is judged based on whether an integrated value of said sensor current reaches a predefined termination judgment value.

6. The control device for an exhaust gas sensor of an internal-combustion engine according to claim 1, wherein the microcomputer:
applies to said sensor element a reverse current early convergence application voltage, which is directed in the same direction as said positive voltage and greater than said positive voltage by a predefined value, for a predetermined period of time since said negative voltage application is terminated.

7. The control device for an exhaust gas sensor of an internal-combustion engine according to claim 1, wherein the microcomputer:

acquires the temperature of said sensor element at the beginning of warm-up for the sensor element; and inhibits the application of said negative voltage during a warm-up process if the temperature of said sensor element is higher than a predefined adsorbable species adsorption temperature at the beginning of warm-up.

8. The control device for an exhaust gas sensor of an internal-combustion engine according to claim 1, wherein the microcomputer:

acquires the temperature of said sensor element at the beginning of warm-up for the sensor element;

applies said positive voltage to said sensor element and judging whether said sensor output suffers predefined rich displacement if the temperature of said sensor element is higher than a predefined adsorbable species judgment temperature at the beginning of warm-up; and inhibits the application of said negative voltage during a warm-up process if said rich displacement is not encountered.

9. The control device for an exhaust gas sensor of an internal-combustion engine according to claim 1, wherein the microcomputer supplies predefined electrical power to said heater using open control for a period of time during which said positive voltage is not applied to said sensor element within a warm-up process for said sensor element.

10. The control device for an exhaust gas sensor of an internal-combustion engine according to claim 1, wherein the microcomputer:

acquires a sensor current that flows upon application of said negative voltage; and acquires said sensor current at a smaller gain upon application of said negative voltage than upon application of said positive voltage.

11. The control device for an exhaust gas sensor of an internal-combustion engine according to claim 1, wherein the microcomputer:

periodically executes impedance detection procedure in which an applied voltage to the sensor element is increased and decreased while an element impedance is detected based on a relationship between a sensor current and the applied voltage, until the temperature of the sensor element reaches said reaction start temperature after the internal-combustion engine startup.

\* \* \* \* \*